United States Patent
Yamasaki et al.

(10) Patent No.: US 7,163,772 B2
(45) Date of Patent: *Jan. 16, 2007

(54) ORGANIC ELECTROPHOTOGRAPHIC PHOTO-RECEPTOR

(75) Inventors: Yasuhiro Yamasaki, Neyagawa (JP); Kenji Takaki, Yawata (JP)

(73) Assignee: Orient Chemical Industries, Ltd., Osaka (JP)

( * ) Notice: Subject to any disclaimer, the term of this patent is extended or adjusted under 35 U.S.C. 154(b) by 235 days.

This patent is subject to a terminal disclaimer.

(21) Appl. No.: 10/750,828

(22) Filed: Jan. 5, 2004

(65) Prior Publication Data

US 2004/0146793 A1 Jul. 29, 2004

(30) Foreign Application Priority Data

Jan. 6, 2003 (JP) .............................. 2003-000523

(51) Int. Cl.
*G03G 5/047* (2006.01)
*G03H 5/06* (2006.01)

(52) U.S. Cl. .................. 430/59.5; 430/59.4; 430/78; 430/133; 540/123; 540/125; 540/128; 540/139; 540/140

(58) Field of Classification Search ................ 430/78, 430/59.4, 59.5, 133; 540/123, 125, 128, 540/139, 140
See application file for complete search history.

(56) References Cited

U.S. PATENT DOCUMENTS 4,719,613 A 1/1988 Hirose et al.
5,039,798 A 8/1991 Johnson
6,017,666 A 1/2000 Nealey et al.
2003/0082469 A1 5/2003 Tamura
2004/0091742 A1 5/2004 Yamasaki et al.

FOREIGN PATENT DOCUMENTS

| EP | 1004634 A2 | 5/2000 |
| JP | 2-73871 A | 3/1990 |
| JP | 4-184452 A | 7/1992 |
| JP | 04362653 A | * 12/1992 |
| WO | WO0150199 A1 | 7/2001 |

OTHER PUBLICATIONS

Borsenberger, Paul M et al. Organic Photoreceptors for Imaging Systems. New York: Marcel-Dekker, Inc. (1993) pp. 289-296.*
English language abstract of JP04351673 A (Dec. 7, 1992).
U.S. Appl. No. 10/701,610, filed Nov. 6, 2003, 1623.
U.S. Appl. No. 10/516,884, Dec. 3, 2004, Unknown.

* cited by examiner

*Primary Examiner*—Christopher Rodee
(74) *Attorney, Agent, or Firm*—Birch, Stewart, Kolasch & Birch, LLP

(57) ABSTRACT

The present invention provides an organic electrophotographic photo-receptor having a conductive substrate and a photosensitive layer laid on the conductive substrate, wherein the photosensitive layer contains at least one μ-oxo bridged heterometal compound as a charge generating material. The organic electrophotographic photo-receptor has high photo-sensitivity, high stability, excellent durability on sensitivity and on electric potential, and has excellent organic photo-conductive property.

10 Claims, 9 Drawing Sheets

ORGANIC ELECTROPHOTOGRAPHIC PHOTO-RECEPTOR

This Nonprovisional application claims priority under 35 U.S.C. § 119(a) on Patent Application No(s). 2003-000523 filed in JAPAN on Jan. 6, 2003, the entire contents of which are hereby incorporated by reference.

BACKGROUND OF THE INVENTION

1. Field of the Invention

The present invention relates to an electrophotographic photo-receptor. In particular, the present invention relates to an organic electrophotographic photo-receptor including a novel μ-oxo bridged heterometal compound as a charge generating material.

2. Description of the Related Art

In an apparatus for image-forming in electrophotographic field such as a copying machine or a printer, an organic photo-receptor having sensitivity for a particular wavelength range generated from a light source of the apparatus has been used. Known organic photo-receptor includes a monolayered form photo-receptor and a multi-layered form photo-receptor. The mono-layered form photo-receptor generally has a thin layer of binding resin, which contains charge generating material and charge transporting material dispersed therein. The multi-layered form photo-receptor generally comprises two layers, i. e., a charge generating layer containing a charge generating material and a charge transporting layer containing a charge transporting material.

Organic photo-conductive substances having sensitivity around a wavelength of 780 nm which is an oscillation wavelength range of a semiconductor laser have been noted as charge generating materials (CGM). A number of organic photo-condudtors (OPC) including such organic photo-conductive substances used as a charge generating material have been proposed. For example, organic photo-condudtors employing titanylphthalocyanine compounds as charge generating materials have been practically used. Organic photo-receptors having high sensitivity, high stability and good durability are strongly desired according with digitalization and speeding up of a copying machine or a printer.

Phthalocyanine compounds and naphthalocyanine compounds have various polymorph (form of crystalline structures) due to its frame structure, and have various electric properties caused by metal-free phthalocyanine/naphthalocyanine or the kinds of central metal of metal Phthalocyanine/naphthalocyanine. Also, the electric properties of the phthalocyanine compounds and naphthalocyanine compounds can vary greatly depending on a process for producing and treating these compounds. In addition, the electric properties of the compounds can vary greatly depending on stacking state even if they have the same structure. In particular, since the stacking states of an organic compound is determined by its polymorph and the polymorph can change state of electron, especially perturbation of n electron, polymorph is one of important features that significantly effects on properties of electronic material such as organic photo-receptor. Therefore, new polymorph has been searched.

Recently, charge generating materials having high sensitivity and high performance have been searched for adjusting for use of short wavelength of light sources due to prevalence of light-emitting diodes (LED) or for color laser-beam printers (LBP) OPC.

For example, with regard to a mixed crystal of two or more kinds of phthalocyanine compounds, Japanese Patent Kokai Publication No. Hei 2(1990)-272067 discloses a process for preparing a X-form metal-free phthalocyanine composition, which includes the steps of adding titanyl phthalocyanine to metal-free phthalocyanine in an amount of the same or less of metal-free phthalocyanine, and stirring the reactant to induce polymorph. Japanese Patent Kokai Publication No. Hei 4(1992)-351673 discloses an electrophotographic photo-receptor containing a mixed crystal comprising oxytitanium phthalocyanine and at least one kind of hydroxymetal phthalocyanine. Japanese Patent Kokai Publication No. Hei 8(1996)-67829 discloses a phthalocyanine mixed crystal with high γ property, which is prepared by dissolving at least two kinds of phthalocyanine compounds in acid; and adding the resultant solution to a mixture solution of water and an organic solvent having a dielectric constant of 20 or less to precipitate as the phthalocyanine mixed crystal. Japanese Patent Kokai Publication No. 2002-12790 discloses organic electrophotographic photo-receptor including a mixed crystal which comprises at least three kinds of phthalocyanine each having different central substance.

Japanese Patent Kokai Publication No. Hei 4(1992)-184452 discloses a coating composition containing titanyl phthalocyanine and multi-type derivative of phthalocyanine (e. g., μ-oxo bridged aluminum phthalocyanine and gallium phthalocyanine), and an electrophotographic photo-receptor using the same. Further, Japanese Patent Kokai Publication No. Hei 9(1997)-217020 discloses a μ-oxo aluminum phthalocyanine dimer having a new polymorph, and Japanese Patent Kokai Publication No. Hei 10(1998)-88023 discloses a μ-oxo gallium phthalocyanine dimer, and the dimers are used as an electrophotographic photo-receptor. In addition, Japanese Patent Kokai Publication No. Hei 7(1995)-295259 discloses an alkoxy bridged metal phthalocyanine dimer, and the dimer is used as an electrophotographic photo-receptor.

Japanese Patent Kokai Publication No. 2000-219817 discloses a photo-receptor containing a μ-oxo aluminum/gallium phthalocyanine dimer (PcAl—O—GaPc) with high sensitivity and high stability on using as organic photo-conductive material such as high gamma photo-conductive material. However, the phthalocyanine dimer described above has heterometal atoms which are able to have a valence of up to three, so the dimer is different from the compound used for an organic photo-receptor according to the present invention. In addition, the dimer is mixed compounds containing homometal dimer, so the dimer is different from the compound according to the present invention.

SUMMARY OF THE INVENTION

It is an object of the present invention to provide an organic electrophotographic photo-receptor with advantageous high photo-sensitivity and electric properties.

More specifically, the present invention provides an organic electrophotographic photo-receptor having a conductive substrate and a photosensitive layer laid on the conductive substrate, wherein the photosensitive layer contains at least one compound selected from the group consisting of a μ-oxo bridged heterometal phthalo/phthalocyanine compound (formula I), phthalo/naphthalocyanine compound (formula II), naphthalo/phthalocyanine compound (formula III) and naphthalo/naphthalocyanine compound (formula IV) represented by the following formulas I, II, III and IV as a charge generating material:

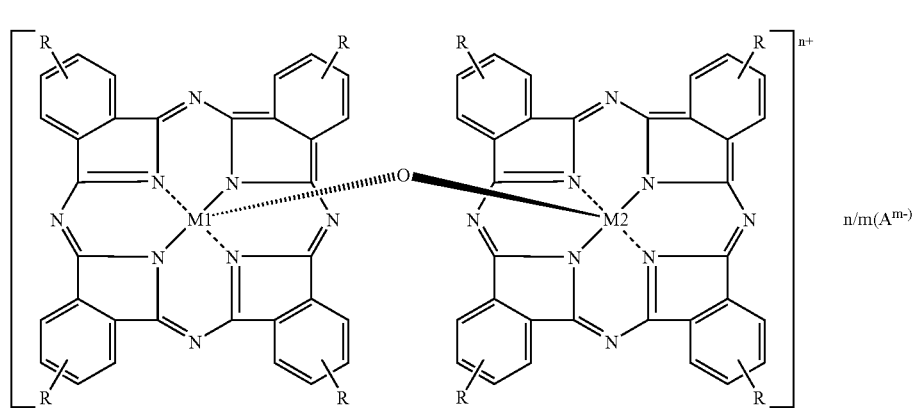
I
n/m(A^{m-})
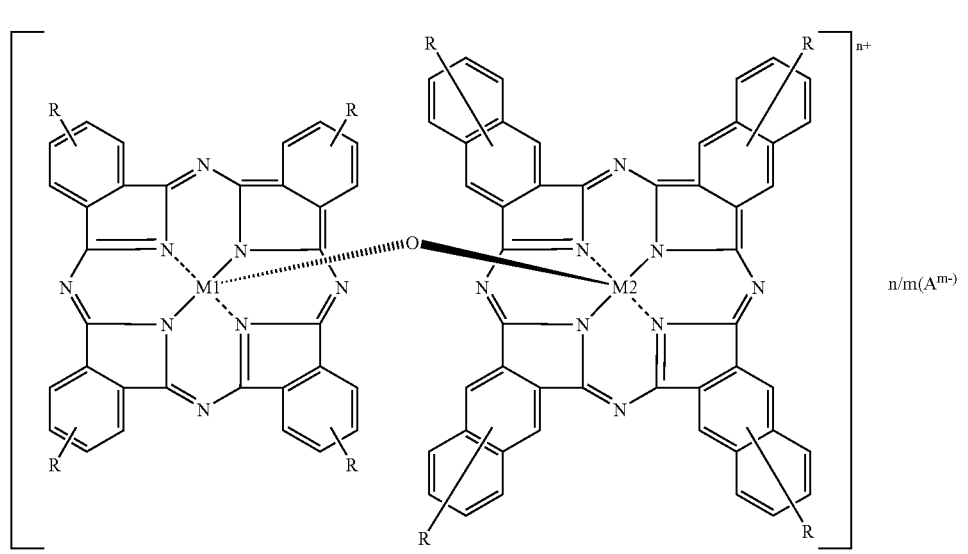
II
n/m(A^{m-})
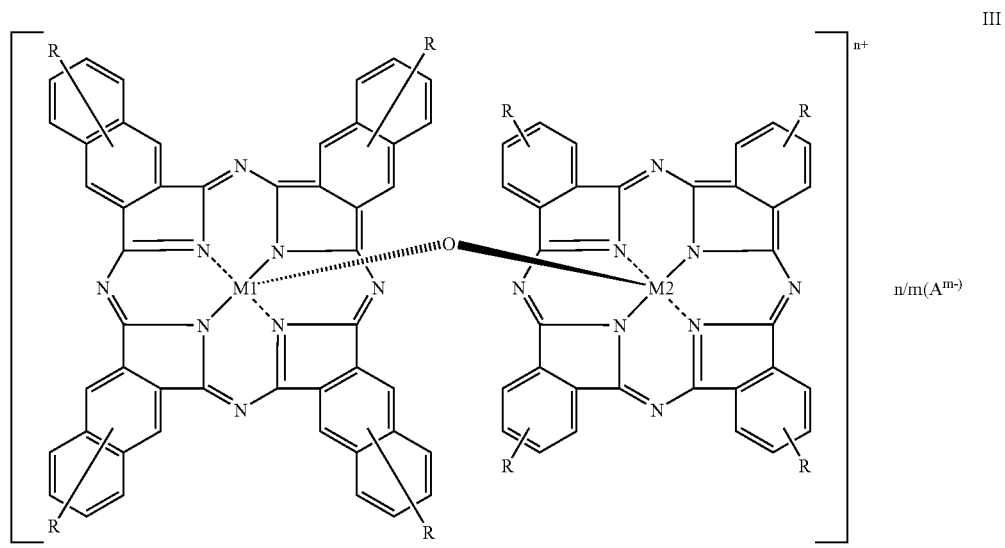
III
n/m(A^{m-})

-continued

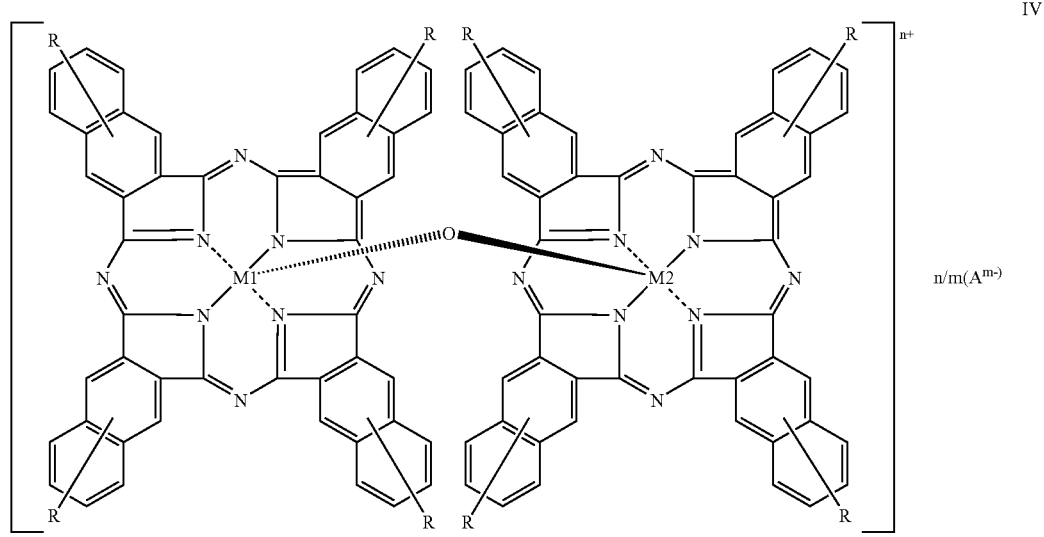

IV

In the formulas I, II, III and IV, M1 represents a metal atom which is able to have a valence of up to three, M2 represents a metal atom which is able to have a valence of four or five, R each independently represents one or more substituent groups and/or substituent atoms, $(A^{m-})$ represents a counteranion A having a valence of m, n/m represents the number of the counteranion, n represents an integer selected from 0 or 1 to 3 corresponding to a valence of M2, and m represents 1 or 2.

In the organic electrophotographic photo-receptor of the present invention, M1 in the above formulas I, II, III and IV is preferably gallium (III) or aluminum (III).

In the organic electrophotographic photo-receptor of the present invention, M2 in the above formulas I, II, III and IV is preferably titanium or vanadium.

In the above formulas I, II, III and IV according to the present invention, M1 should be the atom different from M2. Hereinafter, the above formula I may be represented by "PcM1-O-M2Pc" (e.g., PcGa—O—TiPc), formula II may be represented by "PcM1-O-M2Nc" (e.g., PcAl—O—TiNc), formula III may be represented by "NcM1-O-M2Pc" (e.g., NcGa—O—TiPc), and formula IV may be represented by "NcM1-O-M2Nc" (e.g., NcGa—O—TiNc).

DETAILED DESCRIPTION OF THE PREFERRED EMBODIMENTS

Charge Generating Material (CGM)

Figure 1:
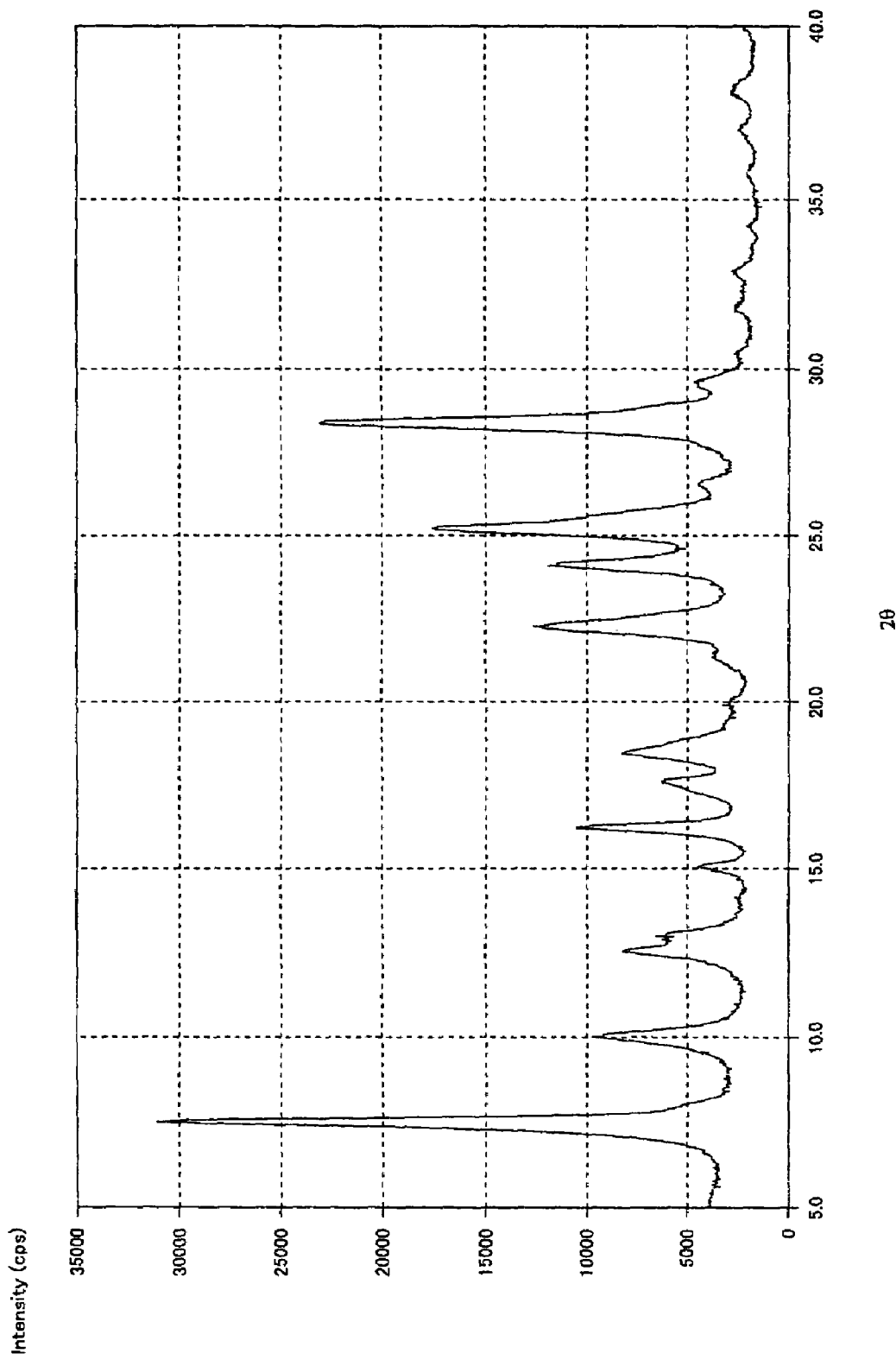
FIG. 1 is an XRD spectrum of a compound (CGM-1A) obtained by Preparation example 1A.

Hereinafter, the term "organic photo-receptor" means organic electrophotographic photo-receptor.

The PcM1-O-M2Nc compound of charge generating material (CGM) has a chemical structure wherein two central metal atoms (M1, M2) are oxo-bridged, M1 being a central metal of a metal phthalocyanine and M2 being a central metal of a metal naphthalocyanine. M1 represents a metal atom which is able to have a valence of up to three and, for example, includes a metal atom of the 3A group (such as Sc and Y) or the 3B group (such as Al, Ga, In and Tl) on the periodic table. M2 represents a metal atom which is able to have a valence of four or five and, for example, includes a metal atom of the 4A to 7A groups, the 8 group and the 4B to 6B groups on the periodic table. A metal atom of the 3A group or the 3B group on the periodic table (such as Al and Ga) is not included in M2. Meanwhile, M2 may exist as a trivalent form when it is included in the structure of the μ-oxo bridged heterometal compound.

M1 which is able to have a valence of up to three includes, e. g., aluminum (Al), gallium (Ga), indium (In). Aluminum and gallium are preferably used as M1. M2 which is able to have a valence of four or five includes, e. g., titanium (Ti), vanadium (Va), molybdenum (Mo), zirconium (Zr), tin (Sn), manganese (Mn), silicon (Si), germanium (Ge). Titanium (Ti) and vanadium (Va) are preferably used as M2, more preferably Titanium (Ti).

A μ-oxo bridged heterometal compound, PcM1-O-M2Pc compound, a PcM1-O-M2Nc compound, an NcM1-O-M2Pc compound or an NcM1-O-M2Nc compound, included in an organic photo-receptor of the present invention, may each have one or more substituent groups and/or substituent atoms (R) on the aromatic rings thereof. The kind of the substituent groups and the substituent atoms is not particularly limited as far as it exists with stability in the compounds, and examples thereof include an alkyl group (such as methyl group, ethyl group, propyl group, isopropyl group, butyl group, tert-butyl group and isoamyl group), an alkoxy group (such as methoxy group, ethoxy group, isopropoxy group and butoxy group), a phenoxy group, an aryl group (such as phenyl group and tolyl group), an aralkyl group (such as benzyl group), an allyl group, an alkenyl group, a cyano group, a halogen atom (such as Cl, Br, I and F), a carboxylate group, a sulfonate group, a nitro group, an amino group, and the like.

In addition, a μ-oxo bridged heterometal compound according to the present invention may carry positive charge (n+) corresponding to a valence of central metal atom (M2) and, therefore, typically exists in a form of being accompanied with a proper counteranion (A) in a solution. Examples of the counteranion (A) include a monovalent inorganic anion such as hydroxy ion (OH$^-$), halogen ion (for example, Cl$^-$) and hydrogen sulfate ion (HSO$_4^-$), or a divalent inorganic anion such as sulfate ion (SO$_4^{2-}$). A preferable counteranion (A) is a hydroxy ion (OH$^-$).

The all μ-oxo bridged heterometal compounds in the organic photo-receptor of the present invention represented by the above formulas I, II, III and IV are novel compounds, and can be prepared as described below.

The μ-oxo bridged heterometal compound can be prepared by reacting a naphthalocyanine having metal halide (III) as central metal thereof (hereinafter, referred to as halometal(III) naphthalocyanine) or a phthalocyanine having metal halide (III) as central metal thereof (hereinafter, referred to as halometal(III) phthalocyanine) with a naphthalocyanine having metal oxide (IV or V) as central metal thereof (hereinafter, referred to as oxymetal(IV or V) naphthalocyanine) or a phthalocyanine having metal oxide (IV or V) as central metal thereof (hereinafter, referred to as oxymetal(IV or V) phthalocyanine) in concentrated sulfuric acid. The preparation process has high selectivity. More preferably, the preparation process includes treating the obtained compounds according to the further process with aqueous ammonia to change $A^{m-}$ for hydroxy ion (OH$^-$) in order to stabilize the corresponding μ-oxo bridged heterometal compound.

For example, a PcGa—O—TiPc compound is an example of the compound represented by the formula I, and is μ-oxo bridged gallium phthalocyanine/titanium phthalocyanine compound. The PcGa—O—TiPc compound can be prepared by reacting 1 mole of chlorogallium phthalocyanine (ClGaPc) (one of the halometal(III) phthalocyanine) with 1 mole of titanyl phthalocyanine (O=TiPc) (one of oxymetal (IV or V) phthalocyanine) in concentrated sulfuric acid at 5° C. for 2 or 3 hours. The reaction mixture is then poured onto large amount of ice-water, dispersed and filtrated. The obtained wet cake is washed and then dispersed in ice-water again, filtrated and washed to obtain a wet cake. The obtained wet cake is dispersed in water and 25 wt % aqueous ammonia to remove an acid residue and to be purified to obtain an object product "{PcGa—O—TiPc}$^+$OH$^-$".

For example, a PcGa—O—TiNc compound is an example of the compound represented by the formula II, and is μ-oxo bridged gallium phthalocyanine/titanium naphthalocyanine compound. The PcGa—O—TiNc compound can be prepared by reacting 1 mole of chlorogallium phthalocyanine (ClGaPc) (one of the halometal(III) phthalocyanine) with 1 mole of titanyl naphthalocyanine (O=TiNc) (one of oxymetal (IV or V) naphthalocyanine) in concentrated sulfuric acid at 5° C. for 2 or 3 hours. The reaction mixture is then poured onto large amount of ice-water, dispersed and filtrated. The obtained wet cake is washed and then dispersed in ice-water again, filtrated and washed to obtain a wet cake. The obtained wet cake is dispersed in water and 25 wt % aqueous ammonia to remove an acid residue and to be purified to obtain an object product "{PcGa—O—TiNc}$^+$OH$^-$".

For example, a NcGa—O—TiPc compound is an example of the compound represented by the formula III, and is μ-oxo bridged gallium naphthalocyanine/titanium phthalocyanine compound. The NcGa—O—TiPc compound can be prepared by reacting 1 mole of chlorogallium naphthalocyanine (ClGaNc) (one of the halometal(III) naphthalocyanine) with 1 mole of titanyl phthalocyanine (O=TiPc) (one of oxymetal (IV or V) phthalocyanine) in concentrated sulfuric acid at 5° C. for 2 or 3 hours. The reaction mixture is then poured onto large amount of ice-water, dispersed and filtrated. The obtained wet cake is washed and then dispersed in ice-water again, filtrated and washed to obtain a wet cake. The obtained wet cake is dispersed in water and 25 wt % aqueous ammonia to remove an acid residue and to be purified to obtain an object product "{NcGa—O—TiPc}$^+$OH$^-$".

For example, a NcGa—O—TiNc compound is an example of the compound represented by the formula IV, and is μ-oxo bridged gallium naphthalocyanine/titanium naphthalocyanine compound. The NcGa—O—TiNc compound can be prepared by reacting 1 mole of chlorogallium naphthalocyanine (ClGaNc) (one of the halometal(III) naphthalocyanine) with 1 mole of titanyl naphthalocyanine (O=TiNc) (one of oxymetal (IV or V) naphthalocyanine) in concentrated sulfuric acid at 5° C. for 2 or 3 hours. The reaction mixture is then poured onto large amount of ice-water, dispersed and filtrated. The obtained wet cake is washed and then dispersed in ice-water again, filtrated and washed to obtain a wet cake. The obtained wet cake is dispersed in water and 25 wt % aqueous ammonia to remove an acid residue and to be purified to obtain an object product "{NcGa—O—TiNc}$^+$OH$^-$".

The treatment, such that reaction products and the like are dissolved in concentrated sulfuric acid, and the solution is poured onto water/ice to precipitate a solid thereof so as to be finely divided and refined, is referred to as "acid pasting treatment". In the present invention, the acid pasting treatment provides the reaction of halometal(III) naphthalocyanine or halometal(III) phthalocyanine with oxymetal(IV or V) naphthalocyanine or oxymetal(IV or V) phthalocyanine to obtain a μ-oxo bridged heterometal compound.

A purification process of the obtained compound includes treatment with aqueous ammonia, which leads to removal of an acid residue from the obtained compound and stabilization of the compound. Specifically, the obtained compound is added to water and ammonia solution and filtrated. The filtrated-out compound is then sufficiently washed with water and ion exchange water, and dried to refine the compound easily. The aqueous ammonia preferably used has a concentration of 1 wt % or more, preferably 5 to 50 wt %, and particularly the aqueous ammonia having a concentration of 25 wt % is preferably used.

The above process provides a preparation of the μ-oxo bridged heterometal compounds included in the organic photo-receptor of the present invention with simplicity, selectively and high yield.

Halometal(III) naphthalocyanine or halometal(III) phthalocyanine and oxymetal(IV or V) naphthalocyanine or oxymetal(IV or V) phthalocyanine are preferably employed in a molar ratio of 1 to 1, namely, equivalent moles to each other. The reason therefor is that the reaction at this molar ratio enables an intended μ-oxo bridged heterometal compound to be selectively obtained with high yield.

The μ-oxo bridged heterometal compound obtained by acid pasting treatment with concentrated sulfuric acid has usually amorphous state. When the μ-oxo bridged heterometal compound is used as a charge generating material in an organic photo-receptor, the compound is preferably employed as a compound with a polymorph showing a specific diffraction peak in a X-ray diffraction spectrum after arranging its crystal state. The arranging of crystal state of the μ-oxo bridged heterometal compound into the compound with a polymorph showing a specific diffraction peak in a X-ray diffraction spectrum provides advantageous high performance of a charge generating materials. A measurement of X-ray diffraction spectrum by CuK α-ray with an X-ray diffraction (XRD) apparatus can be used as a process for measuring X-ray diffraction.

The process for arranging crystal state includes wet milling in certain organic solvent, or simply dispersing in certain organic solvent under heating or at room temperature.

The wording "wet mill" or "wet milling" of the present specification means the process in which the substance is milled in the presence of a solvent. The wording "mill" or "milling" means the treatment of fine dividing solid substance by adding mechanical energy. A milling usually involves the use of a mill medium, on a dispersing machine such as a paint shaker, a ball mill, a sand mill, an attritor, and an automatic mortar. A mill medium such as glass beads, steel beads, zirconia beads, and alumina beads may be employed in the wet milling. The wording "simply disperse" or "simply dispersing" means the process in which the substance is dispersed with stirring into a solvent to be suspended in a solvent as a fine particle.

The solvent which is usable in wet milling or simply dispersing includes, e. g., amide solvent such as dimethylformamide (DMF), dimetyl acetamide, N-methyl pyrrolidone; ketone solvent such as cyclohexanone, diisopropyl ketone, methyl ethyl ketone (MEK) and methyl isobutyl ketone; monohydric alcohol solvent such as methanol, ethanol, propanol, isopropanol, amyl alcohol, hexyl alcohol and octyl alcohol; dihydric alcohol solvent such as ethylene glycol, diethylene glycol and triethylene glycol; glycol ether solvent such as ethylene glycol monomethyl ether, ethylene glycol monoethyl ether, propylene glycol monomethyl ether; polyglyme solvent such as monoglyme, diglyme, triglyme and tetraglyme; ether solvent such as tetrahydrofuran (THF), dioxane, ethyl ether and butyl ether; ester solvent such as ethyl acetate, butyl acetate; aromatic solvent such as toluene, xylenes and tetralin; high boiling aromatic hydrocarbon solvent such as o-dichlorobenzene, chloronaphthalene and quinoline. The solvents may be employed in alone or in combination with two or more solvents.

The wet milling is continued by use of the above solvent until changeing of polymorph does not proceed any more. Generally, the wet milling is continued at room temperature to reflux-temperature of an organic solvent until single polymorph grows.

The simply dispersing is continued by use of the above solvent until changing of polymorph stop proceeding. Generally, the simply dispersing is continued at room temperature to reflux-temperature of an organic solvent until single polymorph grows.

Organic Photo-receptor

An organic photo-receptor of the present invention may be mono-layered form, or multi-layered form having two layers of a charge generating layer (CGL) and a charge transporting layer (CGL). CGL and CTL in a multi-layered photo-receptor do not inhibit the respective functions, and efficiently transfer generated charge to a surface of the electrophotographic photo-receptor without trapping the charge, thus the use of the μ-oxo bridged heterometal phthalo/phthalocyanine compound as a charge generating material brings out effective electric properties and photosensitivity. Thus, it is preferred that the multi-layered photo-receptor is employed in the present invention.

The multi-layered photo-receptor can be produced by forming a charge generating layer and a charge transporting layer in the form of thin-layer on a conductive substrate. The usable conductive substrate includes metals such as aluminum and nickel, metal vapor-depositing film, and the like, in the form of a drum, a sheet or a belt.

The organic photo-receptor can be produced by the following process. A charge generating layer (CGL) containing a charge generating material (CGM, e. g., GaPc-O—TiPc) is formed as a thin layer on the conductive substrate. It can be formed by vapor-depositing the charge generating material, but is generally formed by applying a binder resin dispersion of the charge generating material.

The binder resin dispersion may be prepared by dispersing the charge generating material into a solution of a suitable binder resin, using a usual dispersing apparatus such as ball mill, sand mill, paint shaker, and the like.

A process for coating the binder resin dispersion is not specifically limited, and suitably include bar coating, dip coating, spin coating, roller coating, calendar coating, and the like. The coated layer may be dried at a temperature of 30 to 200° C. for 5 minutes to 2 hours in the presence or absence of blast.

Optional solvent may be employed for preparing the dispersion. The solvent is not particularly limited as far as it solves the optional binder resin. However, the solvent should disperse CGM uniformly and to solve the binder resin. Examples thereof include alcohol solvents such as methanol, ethanol, isopropanol and butanol; aromatic solvents such as toluene, xylenes and tetralin; halogenated solvents such as dichloromethane, chloroform, trichloroethylene and carbon tetrachloride; ester solvents such as ethyl acetate and propyl acetate; ether solvents such as ethylene glycol monoethyl ether, dioxane and tetrahydrofuran; dimethylformamide and dimethyl sulfoxide.

The binder resin can be selected from a wide range of insulating resins. Examples of the preferred resin include condensation-polymerized resins such as polycarbonate, polyester, polyamide and polyarylate; addition-polymerized polymers such as polystyrene, polyacrylate, styrene-acrylic copolymer, polyacrylamide, polymethacrylate, polyvinyl butyral, polyacrylonitrile, polyacrylic-butadiene copolymer, polyvinyl chloride and vinyl chloride-vinyl acetate copolymer; organic photo-conductive resins such as poly-N-vinyl carbazole and polyvinylanthracene; polysulfone, polyether sulfone, silicone resin, epoxy resin and urethane resin. These are used in alone or in combination thereof.

When the organic photo-receptor of the present invention has a multi-layered form which is composed of a charge generating layer and a charge transporting layer, the binder resin is employed in an amount of from 0.01 to 10 ratio by weight, preferably 0.1 to 3.0 by weight based on 1.0 weight of the charge generating material in the charge generating layer. When the amount is more than 10, a concentration of the charge generation decreases, and sensitivity of the photoreceptor layer becomes poor. The charge generating layer is preferably formed in a thickness of up to 10 µm, preferably from 0.5 to 5.0 µm.

When the organic photo-receptor of the present invention has a single-layered form with a single photosensitive layer, the photosensitive layer contains the binder resin, the charge generating material and the charge transporting material. The binder resin used in the photosensitive layer is employed in an amount of from 0.02 to 20 ratio by weight, preferably 0.05 to 5.0 by weight based on 1.0 weight of the charge generating material (CGM). The charge transporting layer is employed in an amount of from 0.02 to 20 ratio by weight, preferably 0.05 to 5.0 by weight based on 1.0 weight of the charge generating material. The photosensitive layer is preferably formed in a thickness of up to 100 µm, preferably from 10 to 50 µm.

When the organic photo-receptor of the present invention has a multi-layered form, the charge transporting layer (CTL) containing the charge transporting material (CTM) is then formed on the charge generating layer (CGL) with a thin layered form. The charge transporting layer with a thin layered form may be formed in the same manner as described above for forming CGL. That is, the charge transporting material is dissolved in a solvent with an optional binder resin, and the resulting solution is uniformly applied on CGL, followed by drying.

The usable charge transporting material in the organic photo-receptor of the present invention includes, e.g., known triarylamine compounds, oxazole derivatives, oxadiazole derivatives, pyrazoline derivatives, hydrazone derivatives, hydrazine derivatives, triazine derivatives, quinazoline derivatives, styryl compounds, styryl triphenylamine compounds, butadiene compounds, carbazole compounds, benzofuran derivatives (compounds).

Examples of the charge transporting materials include the following compounds;

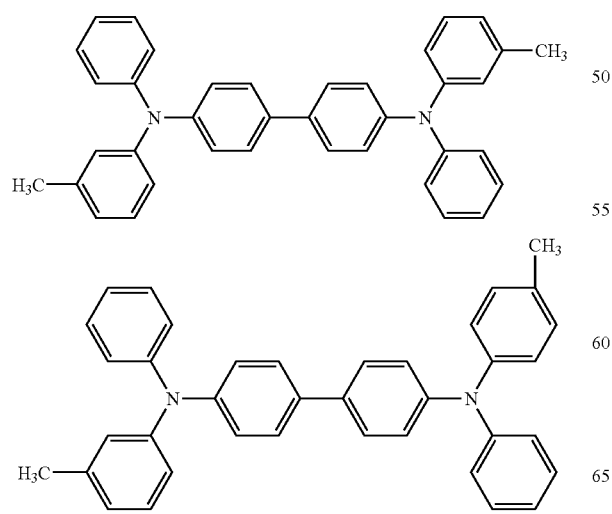

-continued

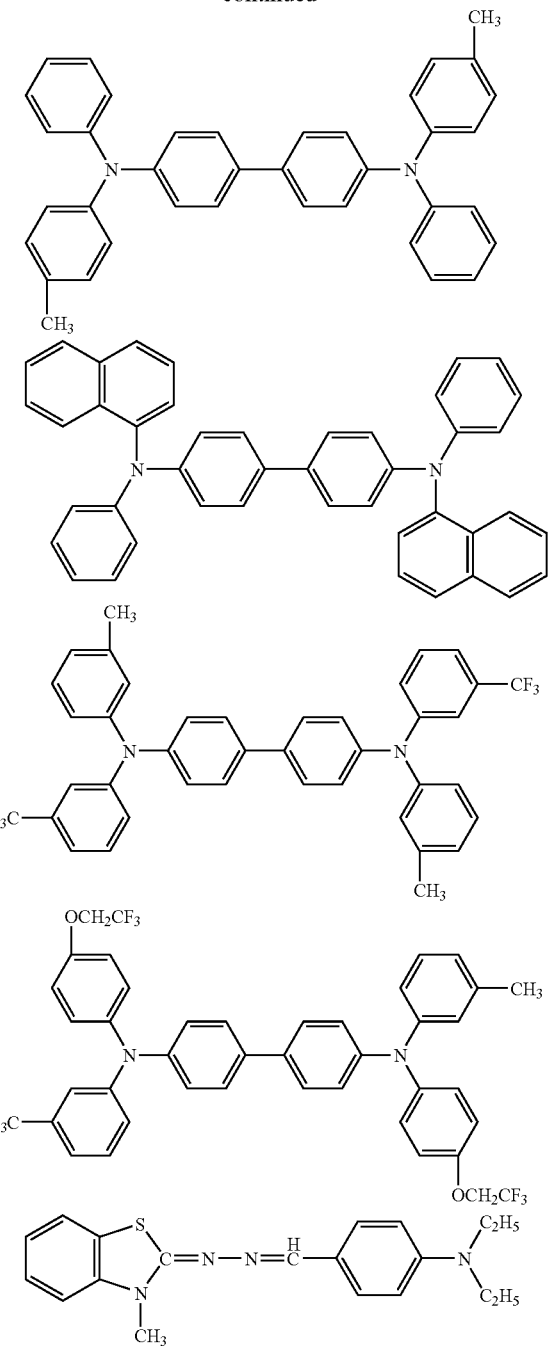

("CT-504"™ commercially available from Fuji Photo Film Co. Ltd.)

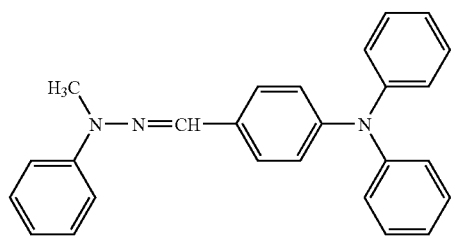

("CT-501"™ commercially available from Fuji Photo Film Co. Ltd.)

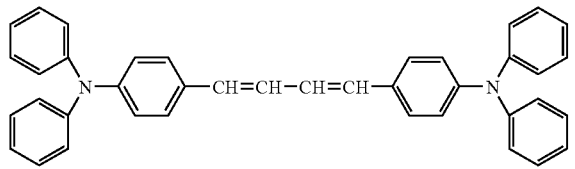

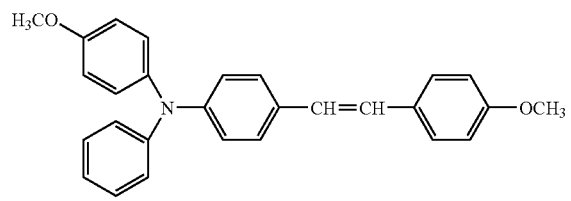

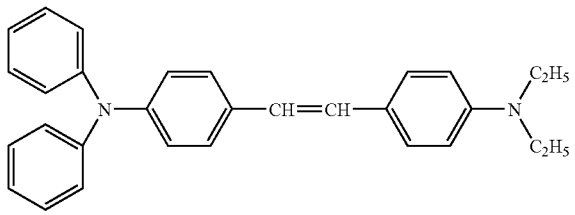

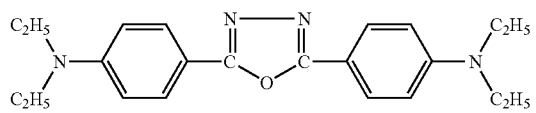

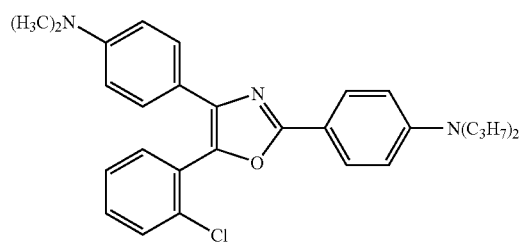

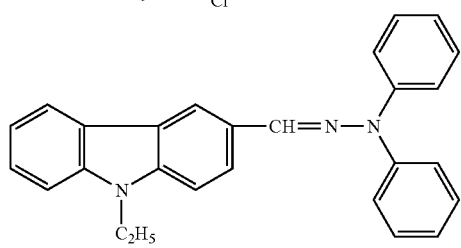

The binder resin and the solvent which are employed for the charge generating layer may be the same as described for the charge transporting layer.

The binder resin for the charge transporting layer is employed in an amount of from 0.1 to 5 ratio by weight based on the charge transporting layer. When the amount is more than 5, concentration of the charge transporting material in the charge transporting layer decreases, and sensitivity of the photo-receptor are deteriorated. The charge transporting layer is preferably formed in a thickness of from 5 to 100 μm, preferably 5 to 70 μm.

Optionally, a protective layer may be formed over the charge generating layer and/or the charge transporting layer. The charge generating layer, the charge transporting layer and/or the protective layer may include various additives, for example, known sensitizers, antioxidants such as amine compounds and phenol compounds, deterioration protectants such as ultraviolet protectants (e. g., benzophenone compounds).

The use of at least one μ-oxo bridged compounds represented by the formulas I, II, III and IV, the μ-oxo bridged heterometal compounds of phthalo/phthalocyanine, phthalo/naphthalocyanine, naphthalo/phthalocyanine and naphthalo/naphthalocyanine, as the charge generating material provides the organic photo-receptor with high stability and excellent durability on sensitivity and on electric potential. The use of the μ-oxo bridged heterometal compounds as the charge generating material provides effective electric properties and photosensitivity. The organic photo-receptor of the present invention has high sensitivity and high stability on using as organic photo-conductive material such as high gamma. Further, the use of the μ-oxo bridged heterometal compounds as the charge generating material provides the organic photo-receptor with characteristics of middle to high sensitivity and spectral sensitivity in shorter wavelength region, as well as longer wavelength region.

The following Examples and Comparative Examples of a charge generating material further illustrate the present invention in detail but are not to be construed to limit the scope thereof. In the present invention, a X-ray diffraction spectrum by CuK α-ray was measured with an automated X-ray diffraction system, MXP3, available from MAC Science Co. Ltd. (The name has been changed to Bruker axs Co. Ltd.)

EXAMPLES

Preparation Example 1

Synthesis of μ-oxo Bridged Heterometal Phthalo/phthalocyanine Compound (PcGa—O—TiPc)

Concentrated sulfuric acid (358 g) was cooled to 5° C. or less and a mixture of 6.1 g (0.010 mole) of chlorogallium phthalocyanine and 5.7 g (0.010 mole) of titanyl phthalocyanine was added thereto with keeping 5° C. or less thereof, and stirred at 5° C. for 2 hours. The mixture was dropped into 600 ml of water and 1400 ml of ice, at 10° C. or less and dispersed for 2 hours. After standing, the mixture was filtrated under reduced pressure, and the obtained wet cake was sprinkled and washed with 2 L of water. The wet cake and 200 ml of water were charged into a 3 L beaker and dispersed at room temperature for 2 hours. After it was filtrated under reduced pressure, the obtained wet cake was sprinkled and washed with 2 L of water. The obtained wet cake, 200 ml of water and 150 ml of 25 wt % aqueous ammonia were charged into a 1 L separable flask and dispersed at room temperature for 6 hours. After it was filtrated under reduced pressure, the obtained wet cake was sprinkled and washed with 2 L of hot water and 1 L of ion exchange water. The wet cake was dried at 70° C. to give 10.7 g of blue solid represented by the following formula (yield, 91.0%).

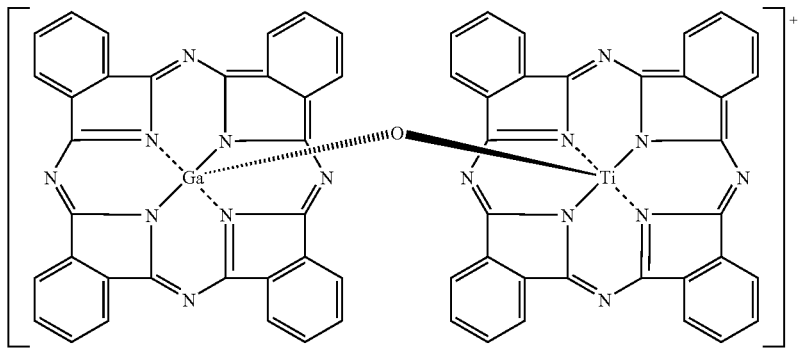

Preparation Example 1A

The obtained compound in preparation example 1, 1.50 g, was added to 20 ml of DMF and stirred at room temperature for 20 hours. The mixture was filtrated, and the obtained wet cake was washed and dried to give 1.28 g of blue solid (CGM-1A). The solid has the polymorph which shows the X-ray diffraction spectrum as showed in FIG. 1.

Preparation Example 1B

Figure 2:
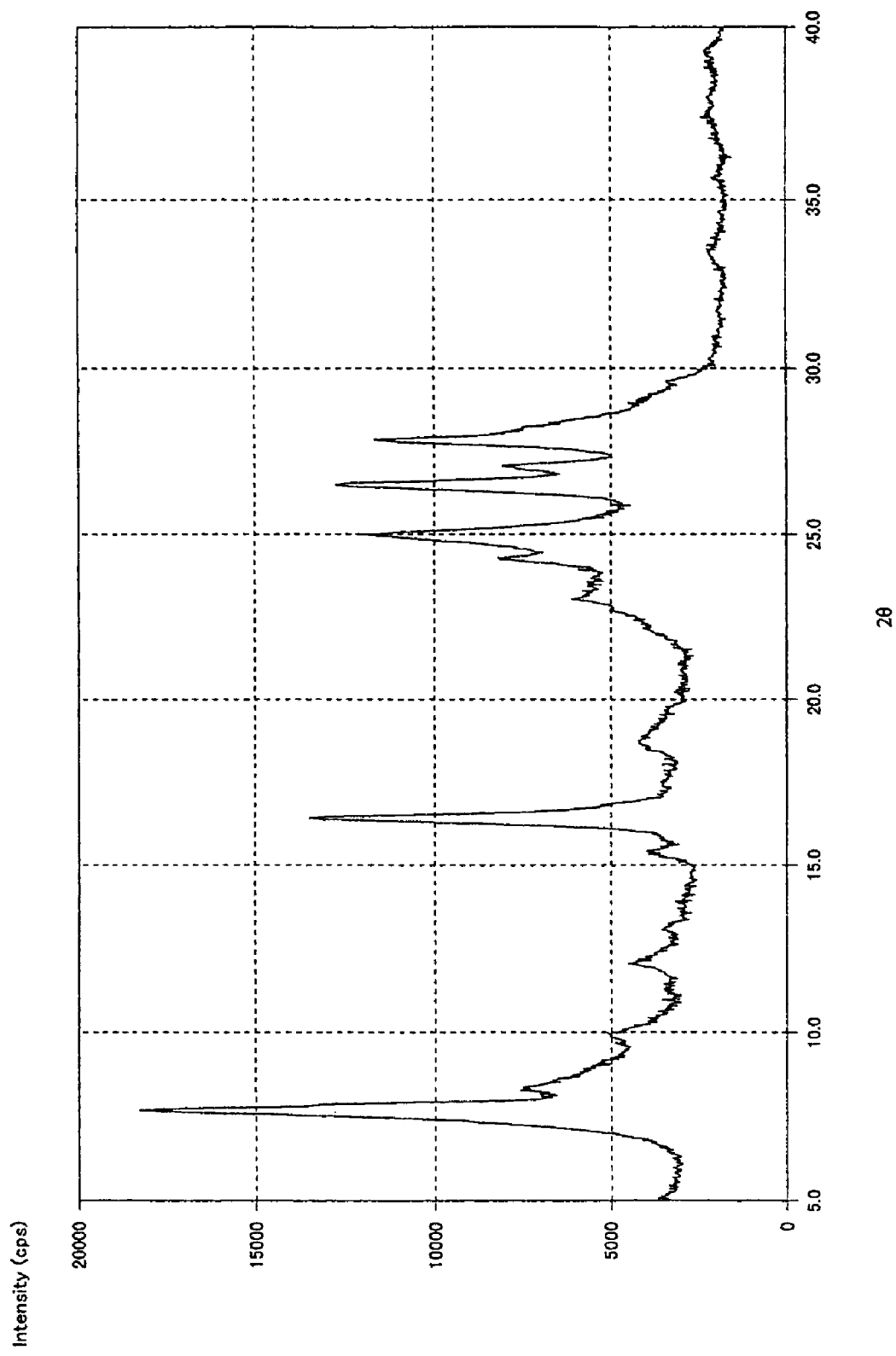
FIG. 2 is an XRD spectrum of a compound (CGM-1B) obtained by Preparation example 1B.

The obtained compound in preparation example 1, 1.24 g, was added to 15 ml of methanol and stirred at room temperature for 22 hours. The mixture was filtrated, and the obtained wet cake was washed and dried to give 1.15 g of blue solid (CGM-1B). The solid has the polymorph which shows the X-ray diffraction spectrum as showed in FIG. 2.

Preparation Example 2

Synthesis of μ-oxo Bridged Heterometal Phthalo/phthalocyanine Compound (PcAl—O—TiPc)

The blue solid represented by following formula was prepared according to substantially the same manner as described in Preparation Example 1, except that chloroaluminum phthalocyanine (0.010 mole) was employed instead of chlorogallium phthalocyanine (0.010 mole) (yield, 84.8% (9.7 g)).

Preparation Example 2A

Figure 3:
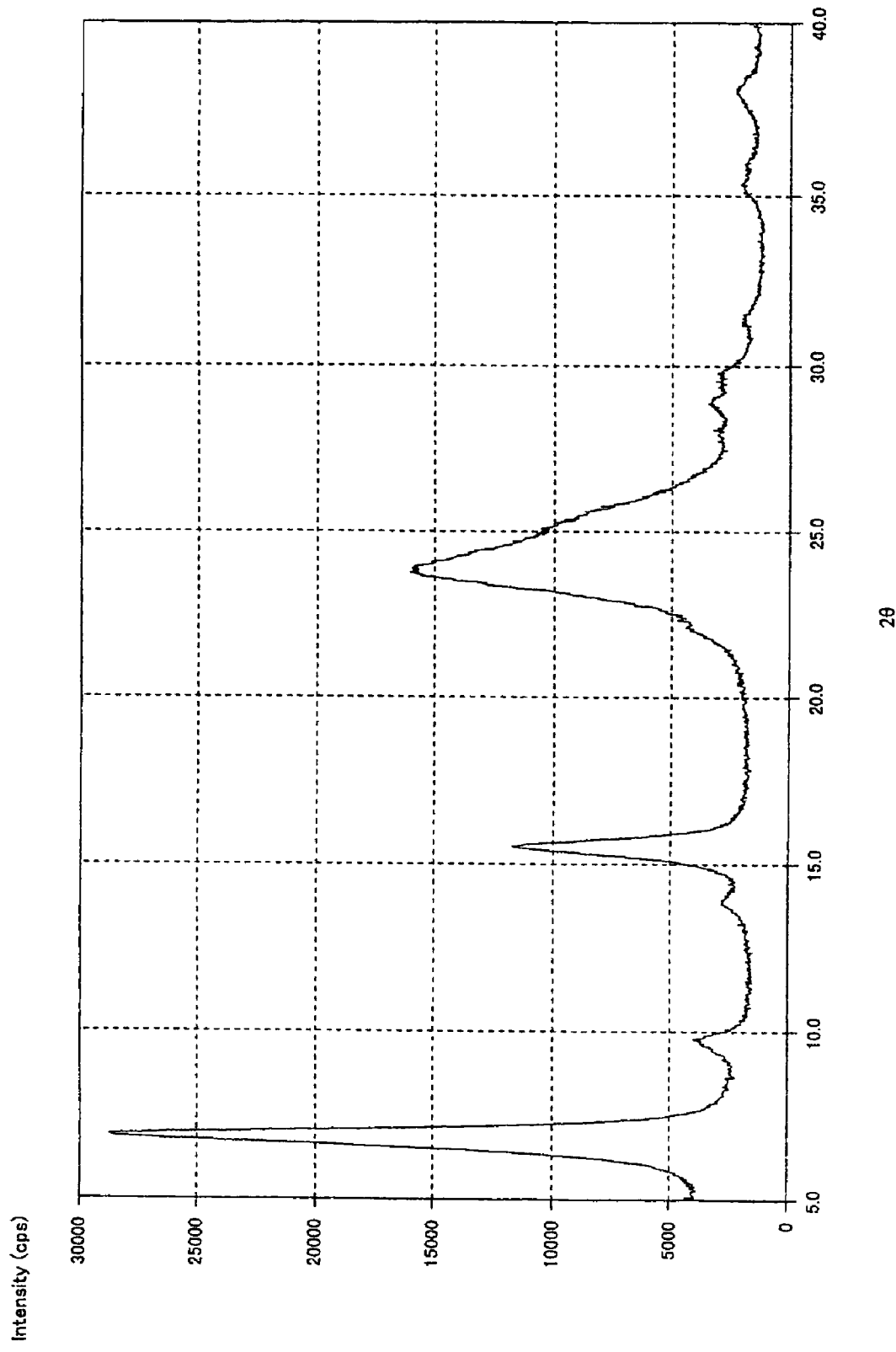
FIG. 3 is an XRD spectrum of a compound (CGM-2A) obtained by Preparation example 2A.

The obtained compound in preparation example 2, 0.91 g, was added to 20 ml of DMF and stirred at room temperature for 15 hours. The mixture was filtrated, and the obtained wet cake was washed and dried to give 0.52 g of blue solid (CGM-2A). The solid has the polymorph which shows the X-ray diffraction spectrum as showed in FIG. 3.

Preparation Example 3

Synthesis of μ-oxo Bridged Heterometal Phthalo/naphthalocyanine Compound (PcGa—O—TiNc)

Concentrated sulfuric acid (44 g) was cooled to 5° C. or less and a mixture of 0.30 g (0.486 mmole) of chlorogallium phthalocyanine and 0.38 g (0.486 mmole) of titanyl naphthalocyanine was added thereto with keeping 5° C. or less thereof, and stirred at 5° C. for 2 hours. The mixture was dropped into 100 ml of water and 300 ml of ice at 10° C. or less and dispersed for 2 hours. After standing, the mixture was filtrated under reduced pressure, and the obtained wet cake was sprinkled and washed with 480 ml of water. The wet cake and 200 ml of water were charged into a 500 ml beaker and dispersed at room temperature for 2 hours. After it was filtrated under reduced pressure, the obtained wet cake was sprinkled and washed with 200 ml of water. The obtained wet cake, 110 ml of water and 66 ml of 25 wt % aqueous ammonia were charged into a 300 ml four-necked

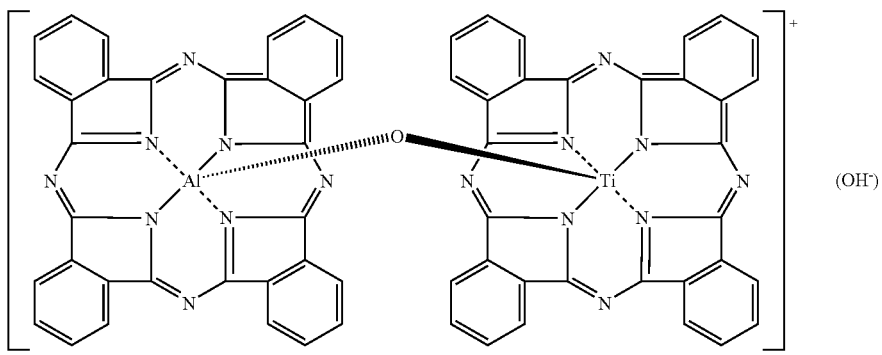

flask and dispersed at room temperature for 6 hours. After it was filtrated under reduced pressure, the obtained wet cake was sprinkled and washed with 350 ml of hot water and 500 ml of ion exchange water. The wet cake was dried at 70° C. to give 0.47 g of blue-green solid represented by the following formula (yield, 70.1%).

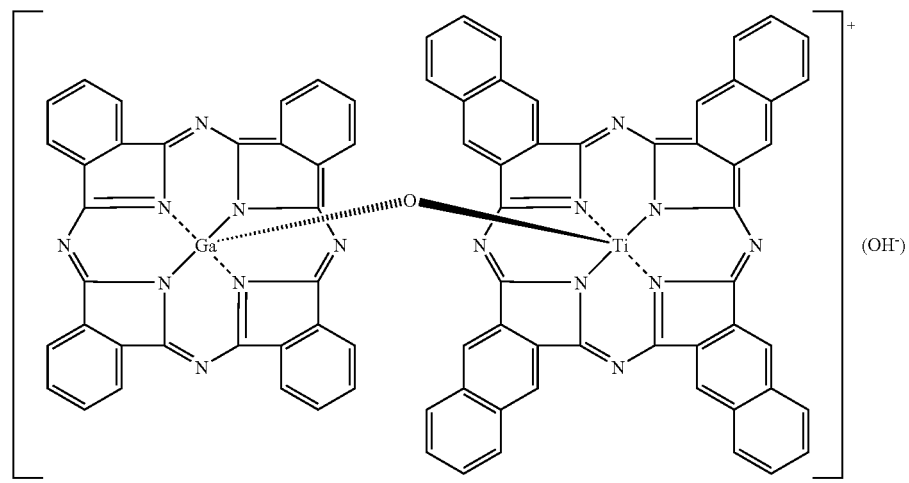

Preparation Example 3A

Figure 6:
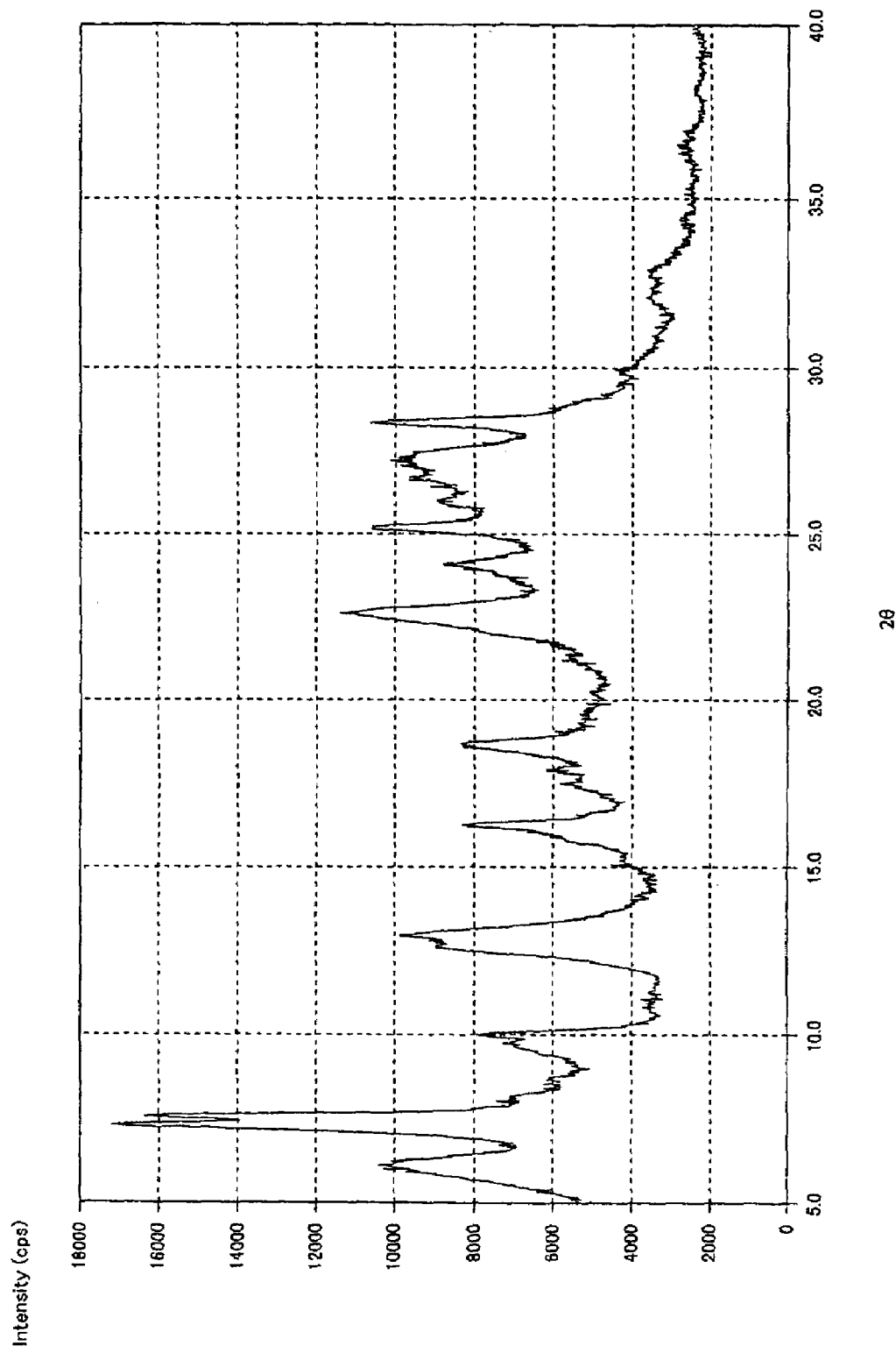
FIG. 6 is an XRD spectrum of a compound (CGM-3A) obtained by Preparation example 3A.

The obtained compound in preparation example 3, 0.44 g, was added to 20 ml of DMF and stirred at room temperature for 35 hours. The mixture was filtrated, and the obtained wet cake was washed and dried to give 0.33 g of blue solid (CGM-3A). The solid has the polymorph which shows the X-ray diffraction spectrum as showed in FIG. 6.

Preparation Example 4

Synthesis of μ-oxo Bridged Heterometal Naphthalo/phthalocyanine Compound (NcGa—O—TiPc)

The blue solid represented by following formula was prepared according to substantially the same manner as described in Preparation Example 3, except that chlorogallium naphthalocyanine (ClGaNc) (0.30 g, 0.367 mmole) and titanyl phthalocyanine (O=TiPc) (0.21 g, 0.367 mmole) was employed instead of chlorogallium phthalocyanine and titanyl naphthalocyanine (yield, 63.4% (0.32 g)).

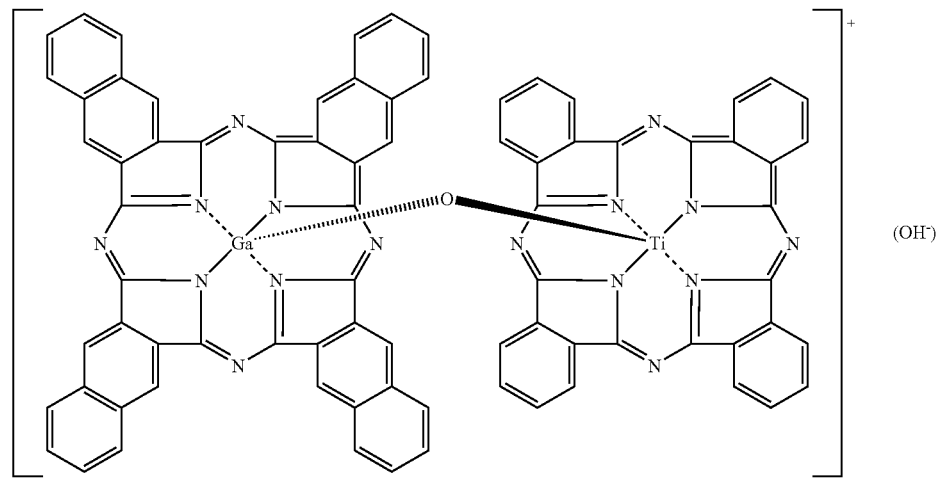

Preparation Example 4A

Figure 5:
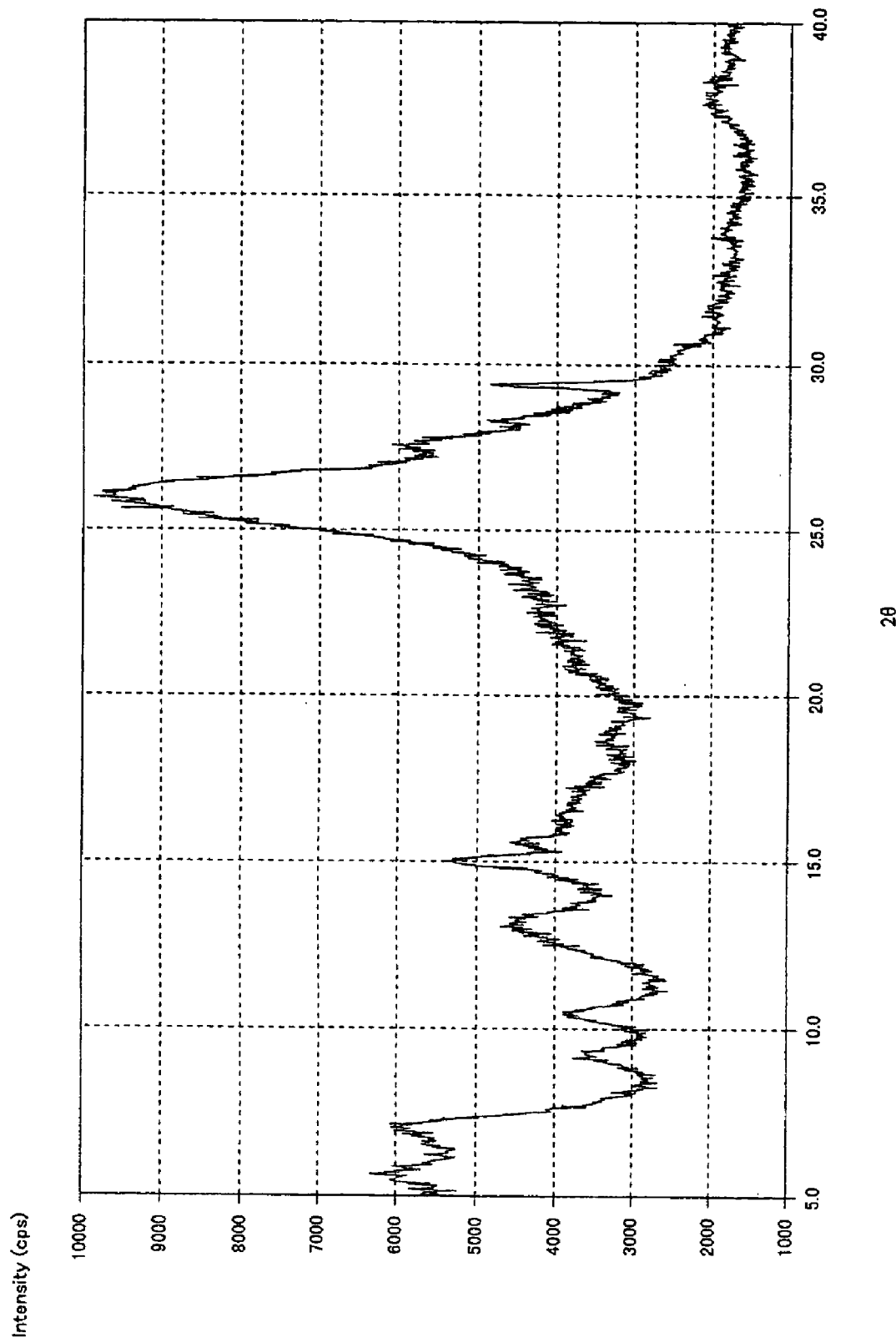
FIG. 5 is an XRD spectrum of a compound (CGM-4A) obtained by Preparation example 4A.

The obtained compound in preparation example 4, 0.29 g, was added to 20 ml of DMF and stirred at room temperature for 37 hours. The mixture was filtrated, and the obtained wet cake was washed and dried to give 0.20 g of black-green solid (CGM-4A). The solid has the polymorph which shows the X-ray diffraction spectrum as showed in FIG. 5.

Preparation Example 5

Synthesis of μ-oxo Bridged Heterometal Naphthalo/naphthalocyanine Compound (NcGa—O—TiNc)

The blue-green solid represented by following formula was prepared according to substantially the same manner as described in Preparation Example 3, except that chloroaluminum naphthalocyanine (ClGaNc) (0.30 g, 0.367 mmole) and titanyl naphthalocyanine (O=TiNc) (0.29 g, 0.367 mmole) was employed instead of chlorogallium phthalocyanine and titanyl naphthalocyanine (yield, 38.1% (0.22 g)).

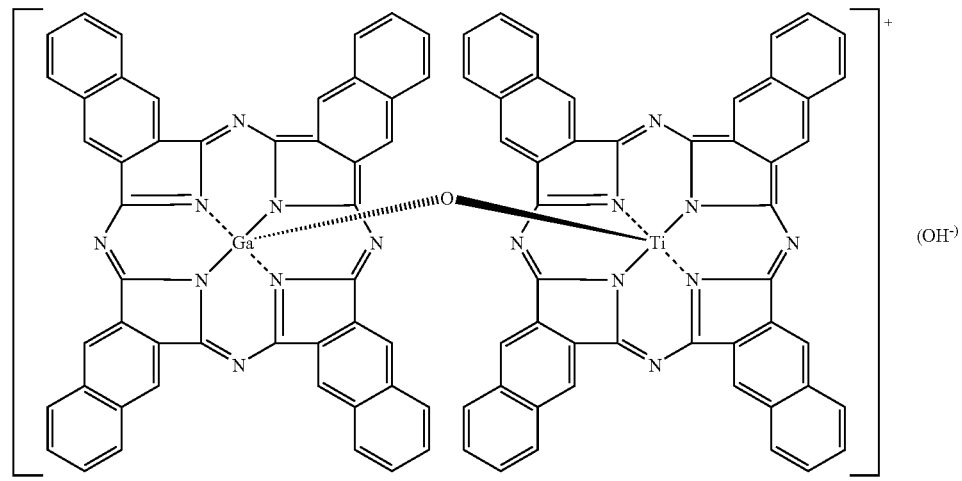

Preparation Example 5A

Figure 4:
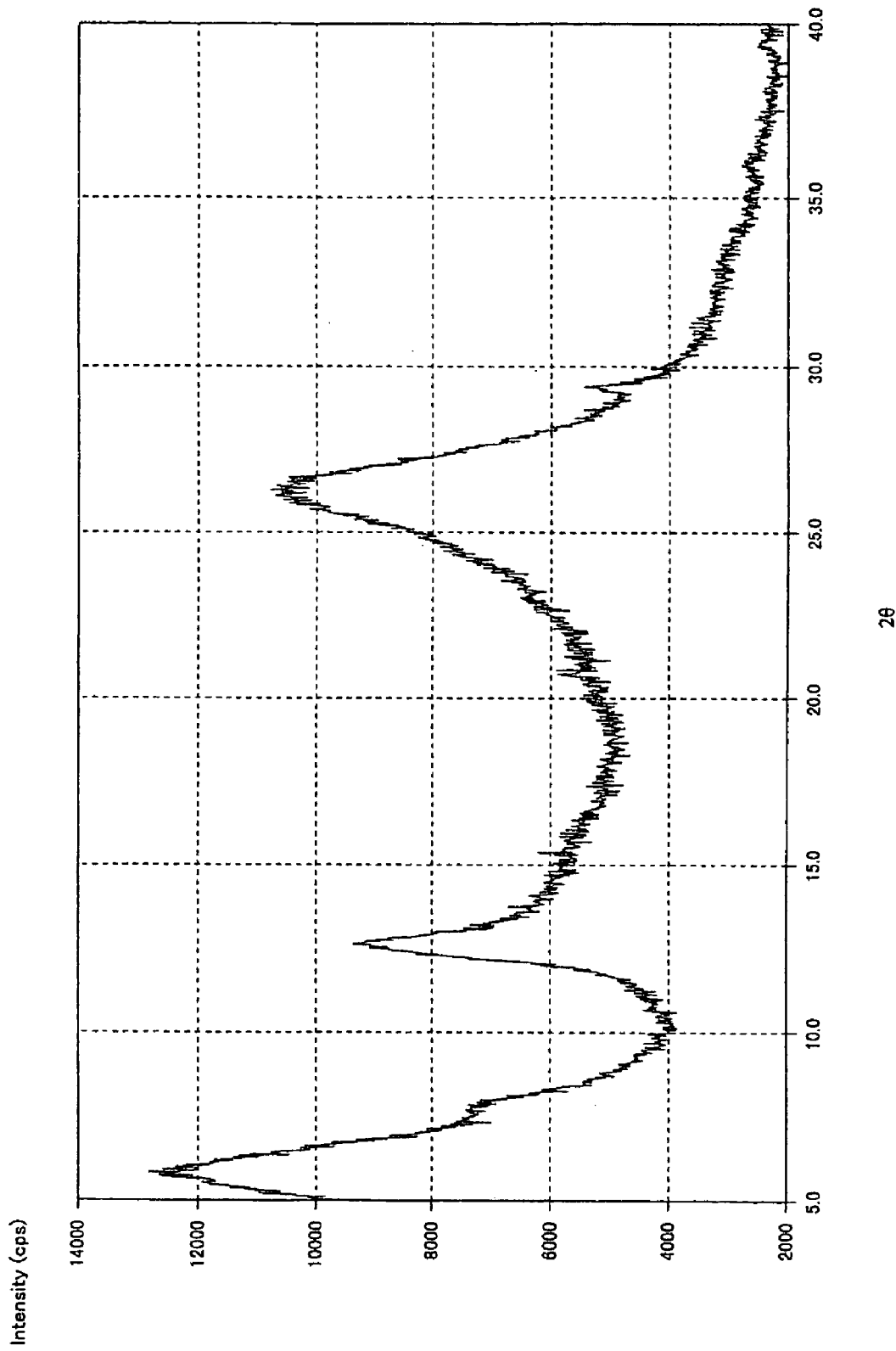
FIG. 4 is an XRD spectrum of a compound (CGM-5A) obtained by Preparation example 5A.

The obtained compound in preparation example 5, 0.19 g, was added to 10 ml of DMF and stirred at room temperature for 34 hours. The mixture was filtrated, and the obtained wet cake was washed and dried to give 0.12 g of black-green solid (CGM-5A). The solid has the polymorph which shows the X-ray diffraction spectrum as showed in FIG. 4.

The solids in the above Production examples were employed as a charge generating material to produce a multi-layered form organic photo-receptor.

Example 1

The μ-oxo bridged heterometal compound prepared in Preparation Example 1A (CGM-1A, PcGa—O—TiPc) (0.2 g), 0.2 g of a polyvinyl butyral resin ("ELEX BH-3"™ commercially available from Sekisui Kagaku K.K.), 59.6 g of cyclohexanone, and 50 g of glass beads having a diameter of 3 mmΦ were charged in a wide-mouthed bottle. The mixture was shook for 1 hour using a dispersing apparatus (paint shaker), and coated on an aluminum plate by a bar coater. The coating was dried in air to form a CGL having a thickness of 0.5 μm.

Then, p-(N,N'-diphenylamino)benzaldehyde-N'-methyl-N'-phenylhydrazine ("CT-501"™ commercially available from Fuji Photo Film Co. Ltd.) (4.5 g), 4.5 g of a polycarbonate resin ("PANLIGHT L-1250"™ commercially available from Teijin K.K.), and 51.0 g of methylene chloride were charged in a wide-mouthed bottle. The mixture was homogenized by using supersonic wave, and coated on the charge generating layer by a bar coater. The coated layer was dried at room temperature to form a charge transporting layer having a thickness of 60 μm. Thereby, a multi-layered form photo-receptor was prepared.

Examples 2 to 6

A layered-form electrophotographic photo-receptor was prepared according to substantially the same manner as described in Example 1, except that the each solid obtained in Preparation Examples 1B to 5A was used as CGM in table 1 instead of the solid obtained in Preparation Example 1A.

The organic photo-receptor's property of the obtained products were measured, and showed in Table 1.

Comparative Example 1

A photo-receptor was produced according to substantially the same manner as described in Example 1, except that a μ-oxo bridged gallium phthalocyanine dimer (G-type dimer described in Japanese Patent Kokai No. Hei 10(1998)-88023) was used as a charge generating material.

Comparative Example 2

A photo-receptor was produced according to substantially the same manner as described in Example 1, except that a μ-oxo bridged aluminum phthalocyanine dimer (II-type dimer described in Japanese Patent Kokai No. Hei 9(1997)-217020) was used as a charge generating material.

Comparative Example 3

A photo-receptor was produced according to substantially the same manner as described in Example 1, except that a μ-oxo bridged heterometal aluminum/gallium phthalocyanine dimer (III-type μ-oxo aluminum/gallium phthalocyanine dimer described in Japanese Patent Kokai No. 2000-219817, example 4) was used as a charge generating material.

Comparative Example 4

A photo-receptor was produced according to substantially the same manner as described in Example 1, except that a X-form metal-free phthalocyanine (H2Pc) was used as a charge generating material.

Evaluation of the Photo-Receptors

Electrophotographic properties (OPC properties) of the photo-receptors prepared in Examples 1 to 6 and Comparative Examples 1 to 4 were measured. A static electricity charging tester "Paper Analyzer EPA-8200" produced by Kawaguchi Denki K. K. was used as the measuring apparatus. The photo-receptors were corona charged at −8.0 kV in STAT 3 mode by first. They were then left in the dark for 2.0 seconds, and irradiated by 5.0 lux white light for 10.0 seconds. The charged potential ($V_{max}$), the photosensitivity for half decay exposure ($E_{1/2}$), the residual potential (Vre), and the dark decay ratio (DDR) (%) were recorded. The results were shown in Table 1 and Table 2.

TABLE 1

| | CGM | CTM | $V_{max}$ (V) | DDR (%) | Vre (V) | $E_{1/2}$ (Lx · s) |
|---|---|---|---|---|---|---|
| Ex. 1 | [PcGa—O—Ti$^+$Pc] OH$^-$ (CGM-1A) | CT-501 | −565.3 | 19.34 | −14.3 | 0.92 |
| Ex. 2 | [PcGa—O—Ti$^+$Pc] OH$^-$ (CGM-1B) | CT-501 | −788.3 | 12.56 | −16.7 | 6.20 |
| Ex. 3 | [PcAl—O—Ti$^+$Pc] OH$^-$ (CGM-2A) | CT-501 | −249.0 | 25.97 | −33.3 | 14.07 |
| Ex. 4 | [NcGa—O—Ti$^+$Nc] OH$^-$ (CGM-5A) | CT-501 | −311.0 | 28.67 | −31.0 | 9.27 |
| Ex. 5 | [NcGa—O—Ti$^+$Pc] OH$^-$ (CGM-4A) | CT-501 | −254.3 | 31.33 | −61.7 | 30.73 |
| Ex. 6 | [PcGa—O—Ti$^+$Nc] OH$^-$ (CGM-3A) | CT-501 | −274.7 | 35.09 | −29.0 | 11.30 |

TABLE 2

| | CGM | CTM | $V_{max}$ (V) | DDR (%) | Vre (V) | $E_{1/2}$ (Lx · s) |
|---|---|---|---|---|---|---|
| Com. Ex. 1 | [PcGa—O—GaPc] | CT-501 | −693.0 | 14.29 | −12.7 | 1.38 |
| Com. Ex. 2 | [PcAl—O—AlPc] | CT-501 | −412.0 | 26.10 | −24.0 | 3.12 |
| Com. Ex. 3 | [PcGa—O—AlPc] | CT-501 | −444.0 | 21.28 | −9.3 | 2.01 |
| Com. Ex. 4 | H2Pc | CT-501 | −774.3 | 12.7 | −18.7 | 2.98 |

The dark decay ratio was determined by measuring a initial charged surface potential ($V_0=V_{max}$) and a surface potential after 2 seconds ($V_2$), and calculating based on the following mathematical formula;

$$DDR(\%)=100\times(V_0-V_2)/V_0$$

Spectral response was determined the followings. The photo-receptors were charged according to the same manner as described in "Evaluation of the Photo-receptors", except that the wavelength of irradiated light was changed between 450 to 900 nm at 50 nm (and 25 nm) intervals. Exposed energy was 1.00 μW. The initial charged potential ($V_{max}$ (V)) and the photosensitivity for half decay exposure ($E_{1/2}$) (μJ/cm$^2$)) at each wavelength were measured. The resultant was shown in FIG. 7.

Durability on electric potential was determined the followings. The photo-receptors were charged according to the same manner with the static electricity charging tester "Paper Analyzer EPA-8200" on durability-measuring mode. The mode re-charged the photo-receptors with 100 times. The obtained change of the charged potential ($V_{max}$) and the photosensitivity for half decay exposure ($E_{1/2}$) was measured. The resultant was shown in FIG. 8 and FIG. 9.

The experimental result shows that the primary property and spectral response of the organic photo-receptor of the present invention have an excellent advantage compared with the properties of μ-oxo bridged gallium phthalocyanine dimer (G-type GPL) of Comparative Example 1, described in Japanese Patent Kokai No. Hei 10(1998)-88023. The μ-oxo bridged heterometal compounds according to the present invention are better suited for a charge generating material with middle to high sensitivity.

Figure 7:
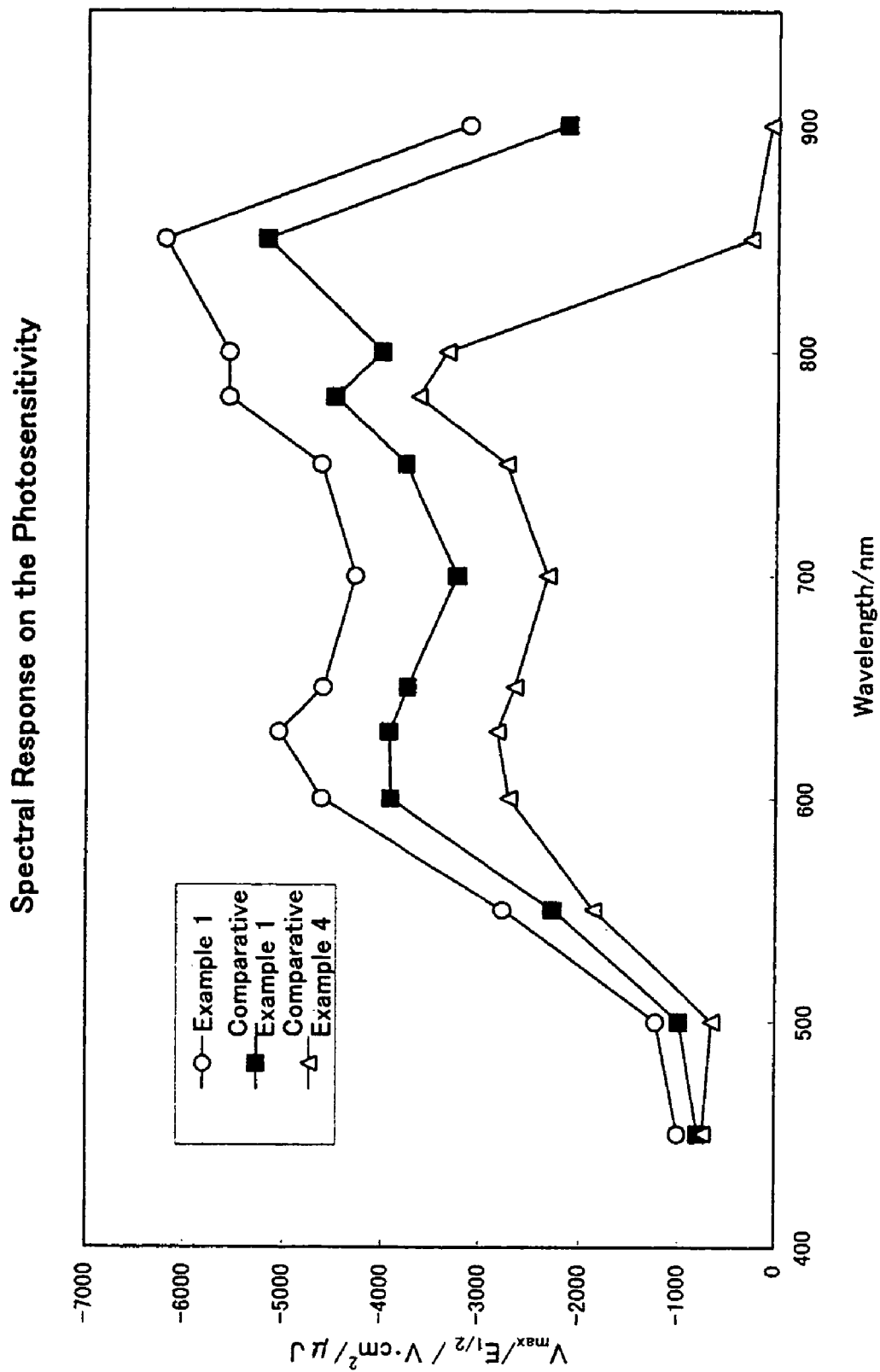
FIG. 7 is a graphic chart showing a spectral response on the photosensitivity of the photo-receptor according to the present invention.
Figure 8:
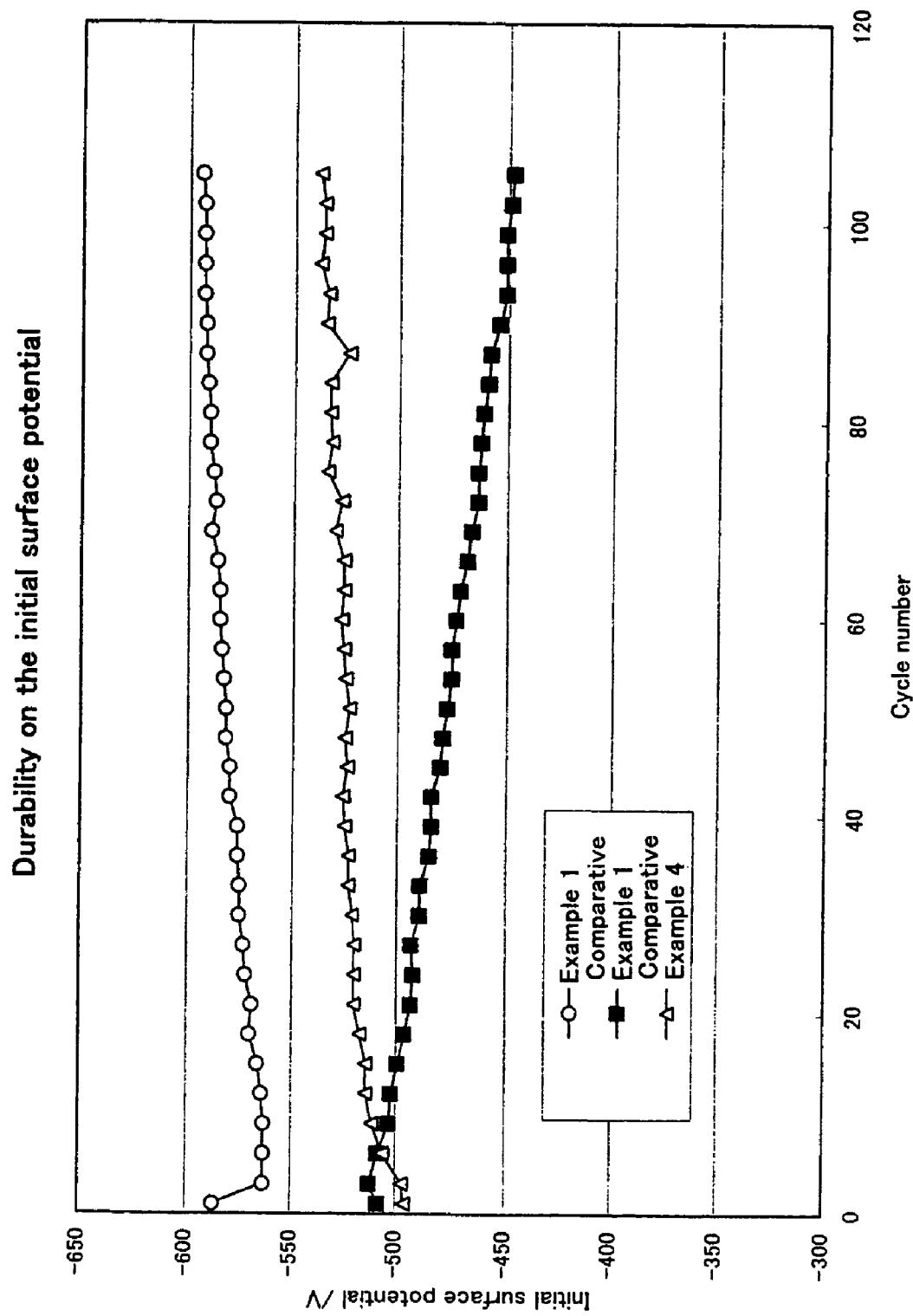
FIG. 8 is a graphic chart showing durability on electric potential of the photo-receptor according to the present invention.
Figure 9:
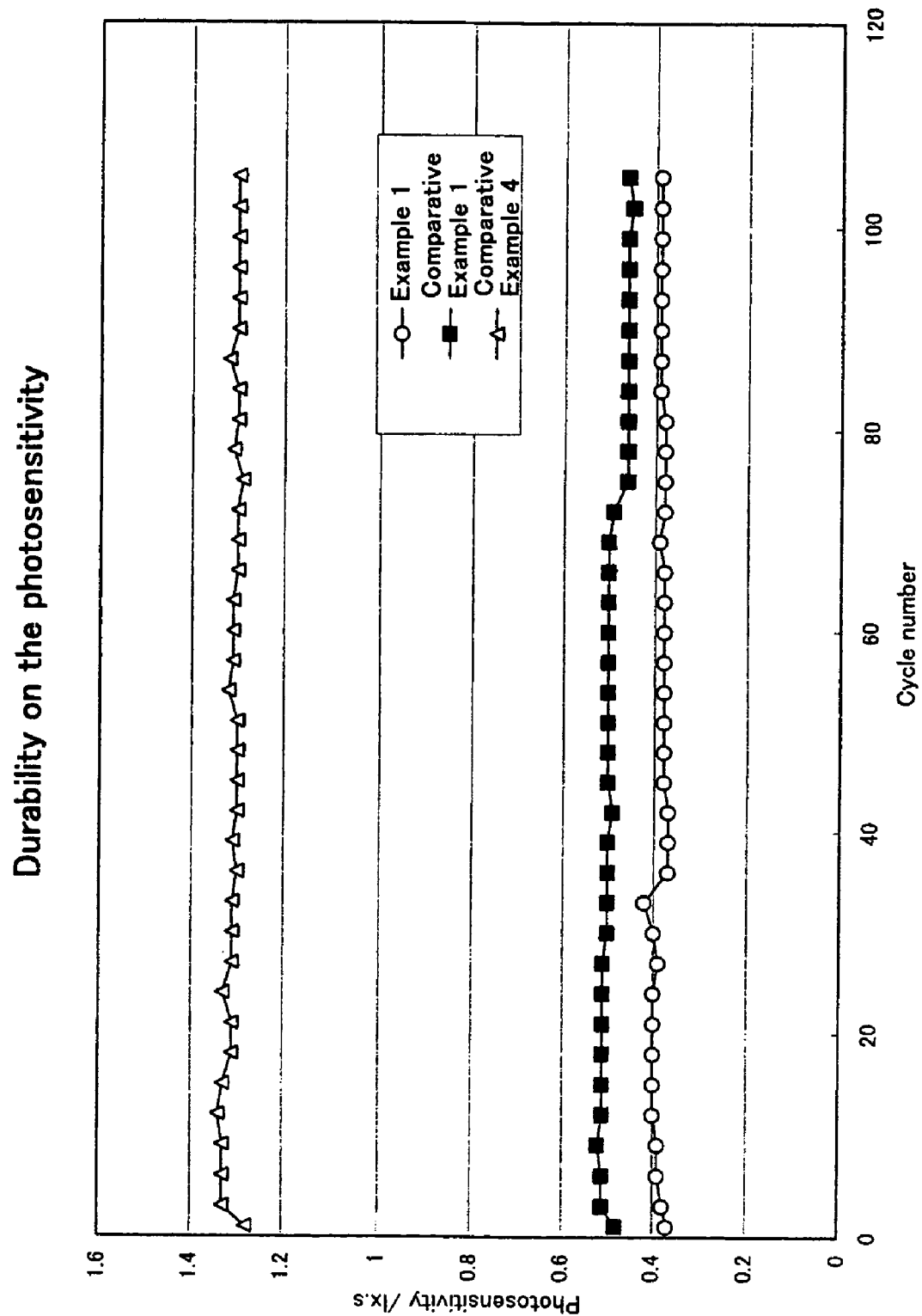
FIG. 9 is a graphic chart showing durability on sensitivity of the photo-receptor according to the present invention.

FIGS. 7 to 9 show that the organic photo-receptor of the present invention containing the μ-oxo bridged heterometal compounds as a charge generating material has high stability, excellent durability on sensitivity and on electric potential, and has excellent organic photo-conductive property.

What is claimed is:

1. An organic electrophotographic photo-receptor having a conductive substrate and a photosensitive layer laid on the conductive substrate, wherein the photosensitive layer contains a μ-oxo bridged heterometal phthalo/phthalocyanine compound represented by the following formula I as a charge generating material:

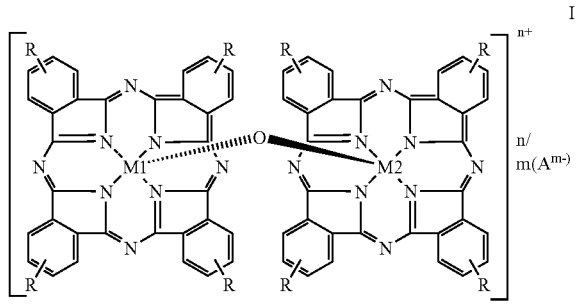

I wherein M1 represents a metal atom which is able to have a valence of up to three, M2 represents a metal atom which is able to have a valence of four or five, R each independently represents one or more substituent groups and/or substituent atoms, ($A^{m-}$) represents a counteranion A having a valence of m, n/m represents the number of the counteranion, n represents an integer selected from 0 or 1 to 3 corresponding to a valence of M2, and m represents 1 or 2.

2. An organic electrophotographic photo-receptor having a conductive substrate and a photosensitive layer laid on the conductive substrate, wherein the photosensitive layer contains a μ-oxo bridged heterometal phthalo/naphthalocyanine compound as a charge generating material represented by the following formula II:

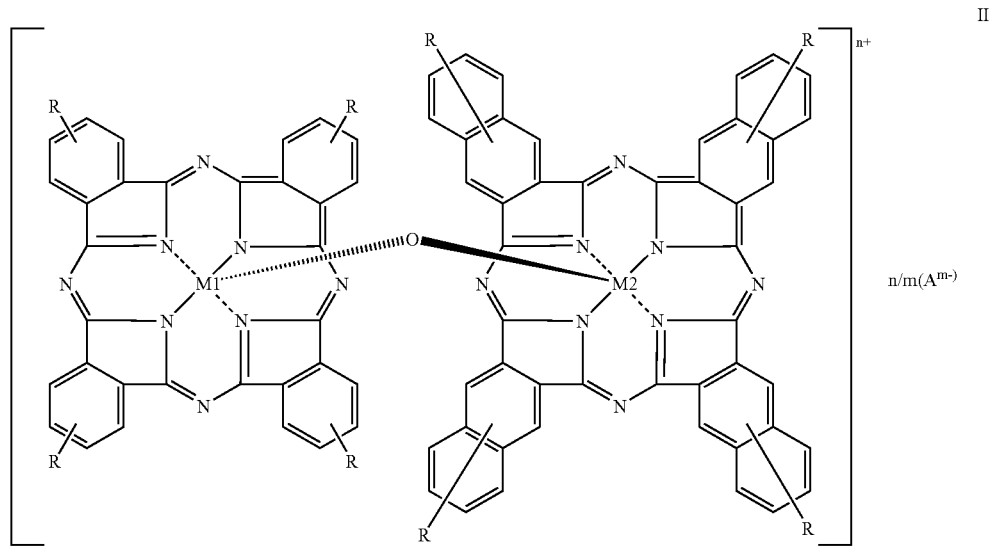

II $n/m(A^{m-})$ wherein M1 represents a metal atom which is able to have a valence of up to three, M2 represents a metal atom which is able to have a valence of four or five, R each independently represents one or more substituent groups and/or substituent atoms, $(A^{m-})$ represents a counteranion A having a valence of m, n/m represents the number of the counteranion, n represents an integer selected from 0 or 1 to 3 corresponding to a valence of M2, and m represents 1 or 2.

3. An organic electrophotographic photo-receptor having a conductive substrate and a photosensitive layer laid on the conductive substrate, wherein the photosensitive layer contains a μ-oxo bridged heterometal naphthalo/phthalocyanine compound represented by the following formula III as a charge generating material:

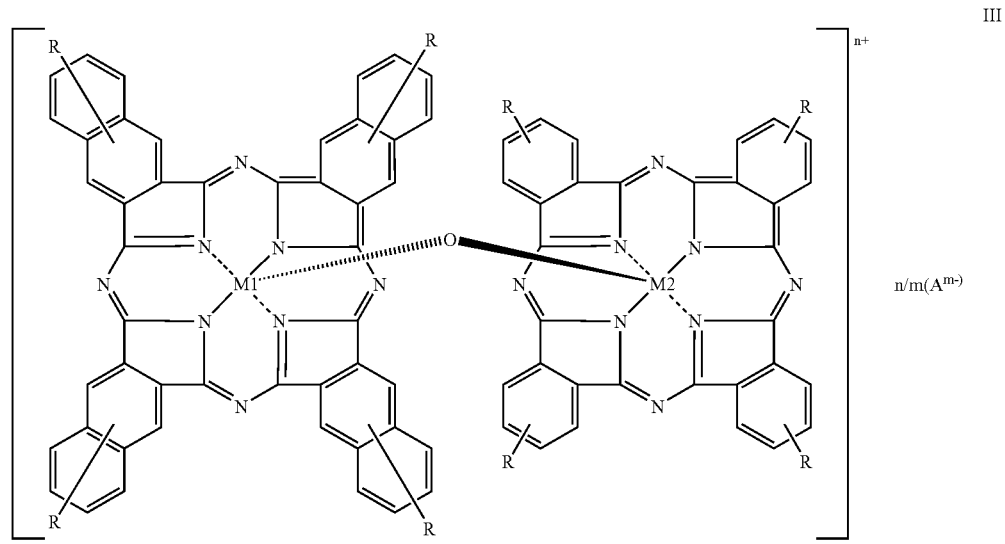

III $n/m(A^{m-})$ wherein M1 represents a metal atom which is able to have a valence of up to three, M2 represents a metal atom which is able to have a valence of four or five, R each independently represents one or more substituent groups and/or substituent atoms, $(A^{m-})$ represents a counteranion A having a valence of m, n/m represents the number of the counteranion, n represents an integer selected from 0 or 1 to 3 corresponding to a valence of M2, and m represents 1 or 2.

4. An organic electrophotographic photo-receptor having a conductive substrate and a photosensitive layer laid on the conductive substrate,
wherein the photosensitive layer contains a µ-oxo bridged heterometal naphthalo/naphthalocyanine compound represented by the following formula IV as a charge generating material:

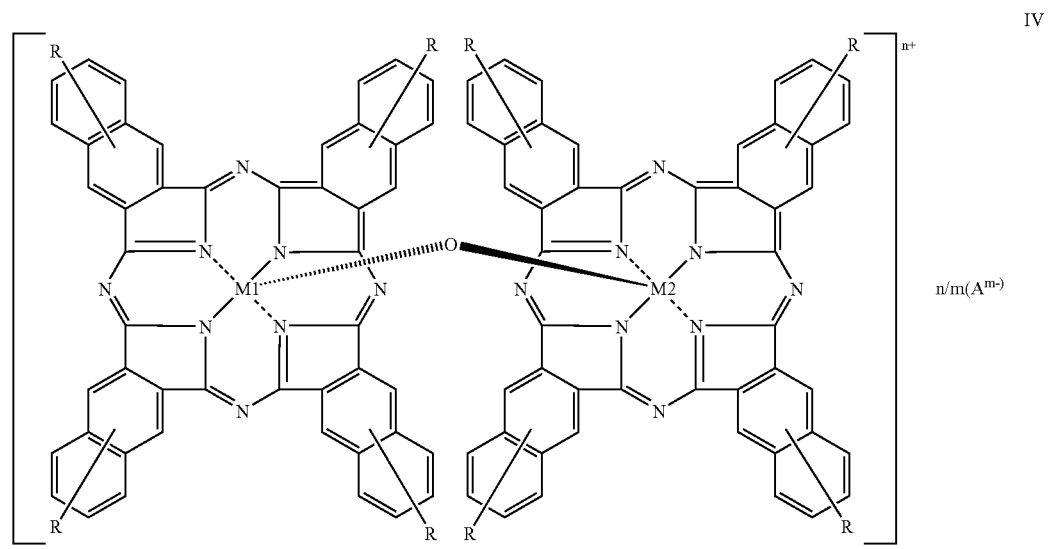

wherein M1 represents a metal atom which is able to have a valence of up to three, M2 represents a metal atom which is able to have a valence of four or five, R each independently represents one or more substituent groups and/or substituent atoms, $(A^{m-})$ represents a counteranion A having a valence of m, n/m represents the number of the counteranion, n represents an integer selected from 0 or 1 to 3 corresponding to a valence of M2, and m represents 1 or 2.

5. The organic electrophotographic photo-receptor according to any one of claims 1 to 4, wherein the M1 is gallium (III) or aluminum (III).

6. The organic electrophotographic photo-receptor according to any one of claims 1 to 4, wherein the charge generating material is a crystal of at least one compounds selected from the group consisting of the µ-oxo bridged heterometal compounds represented by the formulas I to IV in claims 1 to 4, and
the crystal has a polymorph showing a specific diffraction peak in a X-ray diffraction spectrum by CuK α-ray.

7. The organic electrophotographic photo-receptor according to any one of claims 1 to 4, wherein the photosensitive layer has a charge generating layer and charge transporting layer.

8. An organic electrophotographic photo-receptor having a conductive substrate and a photosensitive layer laid on the conductive substrate, wherein the photosensitive layer contains at least one compound selected from the group consisting of μ-oxo bridged heterometal compounds represented by the formulas I to IV:
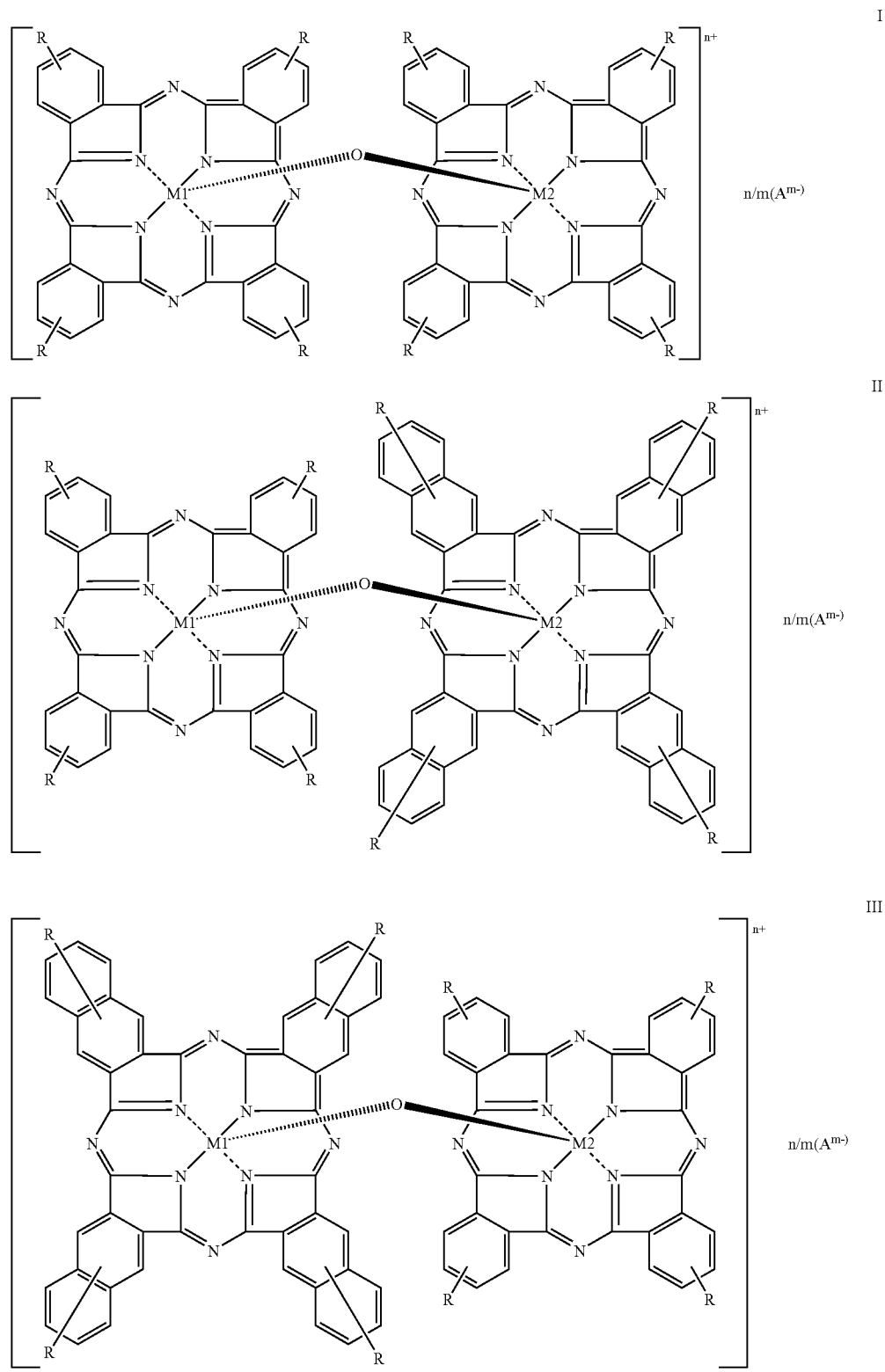

-continued

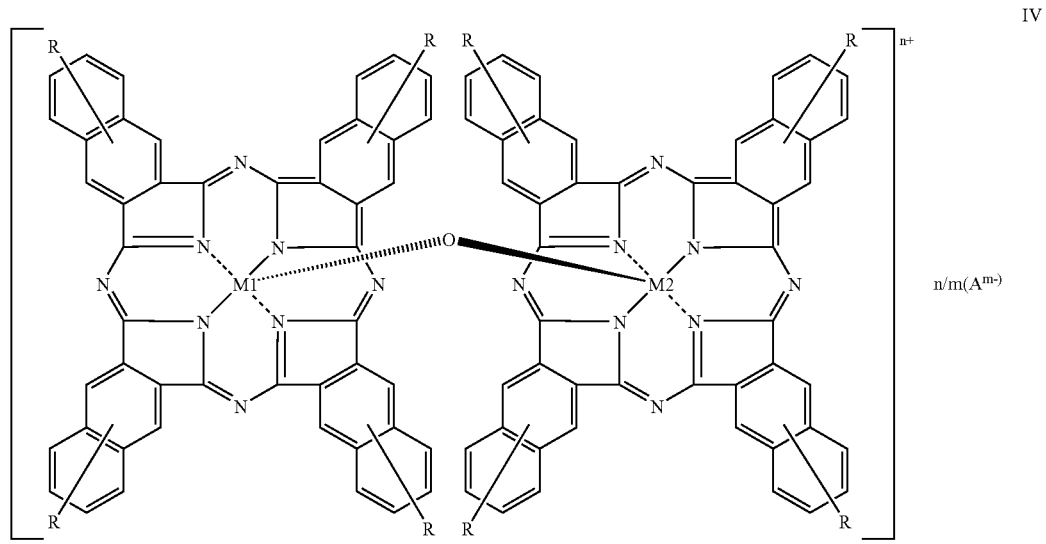

wherein M1 represents a metal atom which is able to have a valence of up to three, M2 represents titanium or vanadium as a metal atom which is able to have a valence of four or five, R each independently represents one or more substituent groups and/or substituent atoms. ($A^{m-}$) represents a counteranion A having a valence of m, n/m represents the number of the counteranion, n represents an integer selected from 0 or 1 to 3 corresponding to a valence of M2, and m represents 1 or 2.

9. A charge generating material for organic electrophotographic photo-receptor comprising at least one compound selected from the group consisting of μ-oxo bridged heterometal compounds represented by the formulas I to IV:

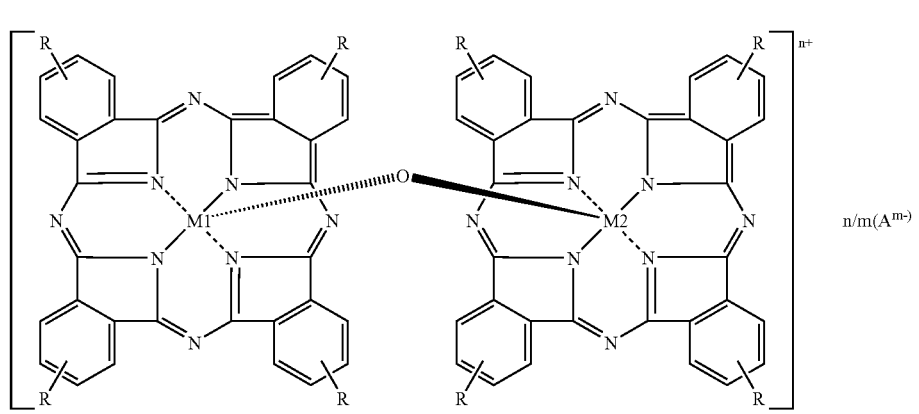

-continued
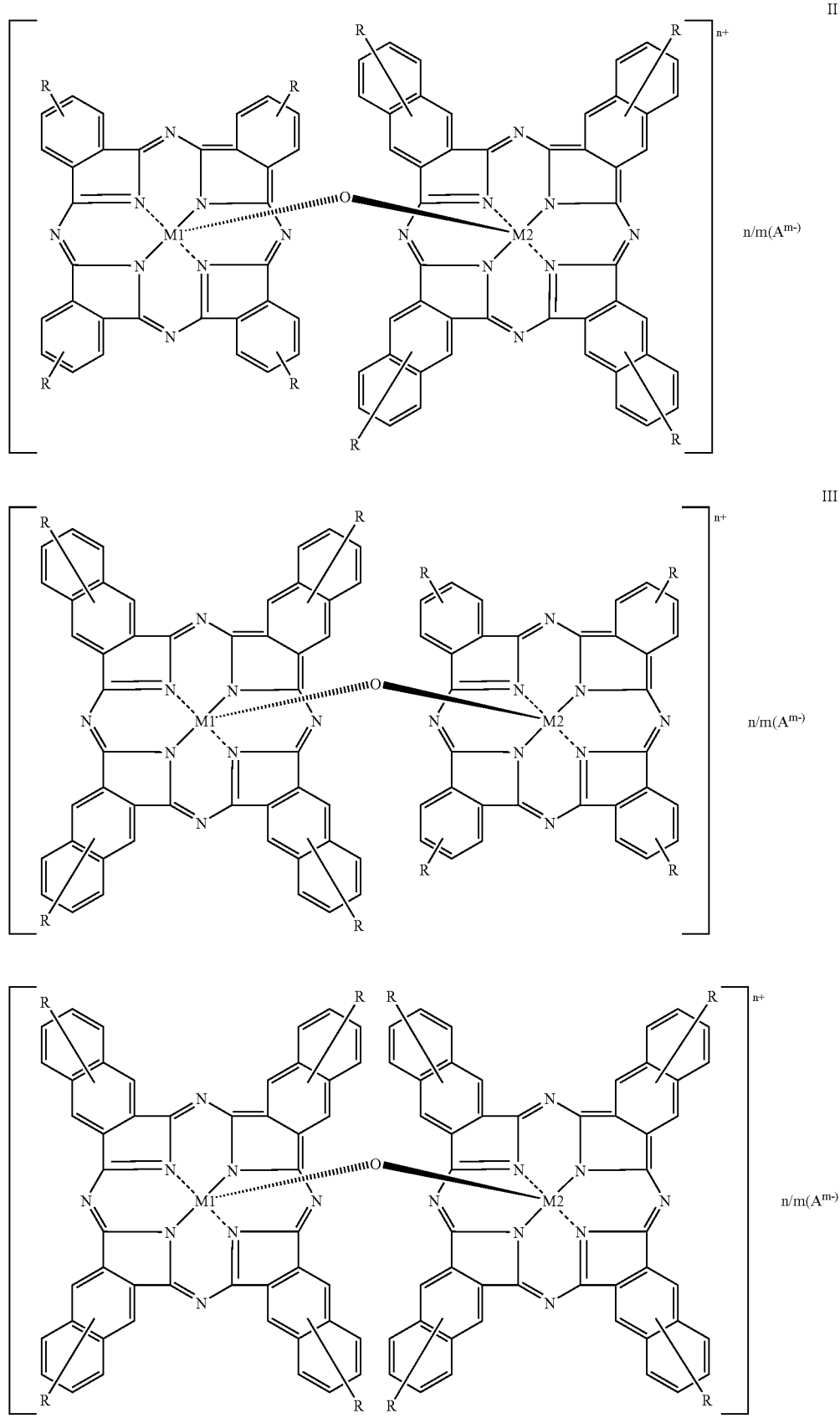

wherein M1 represents a metal atom which is able to have a valence of up to three, M2 represents a metal atom which is able to have a valence of four or five, R each independently represents one or more substituent groups and/or substituent atoms, ($A^{m-}$) represents a counteranion A having a valence of m, n/m represents the number of the counteranion, n represents an integer selected from 0 or 1 to 3 corresponding to a valence of M2, and m represents 1 or 2.

10. A process for preparing an organic electrophotographic photo-receptor comprising the steps of:
forming a charge generating layer containing at least one compound selected from the group consisting of the μ-oxo bridged heterometal compounds represented by the formulas I to IV, on a conductive substrate, and
forming a charge transporting layer on the charge generating layer;

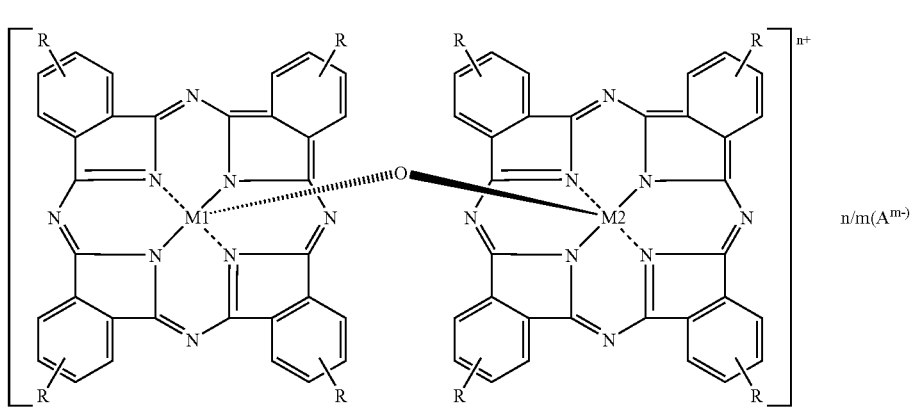

I

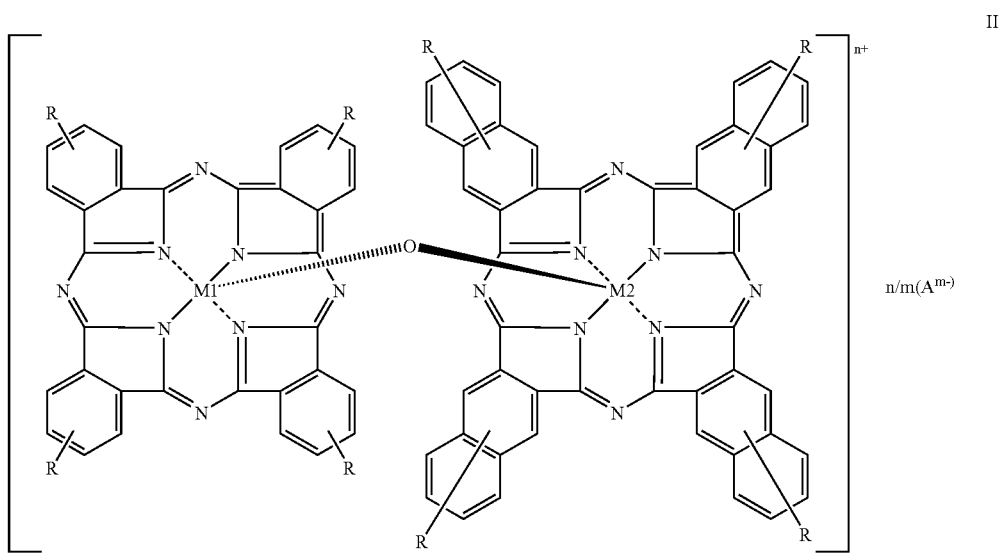

II

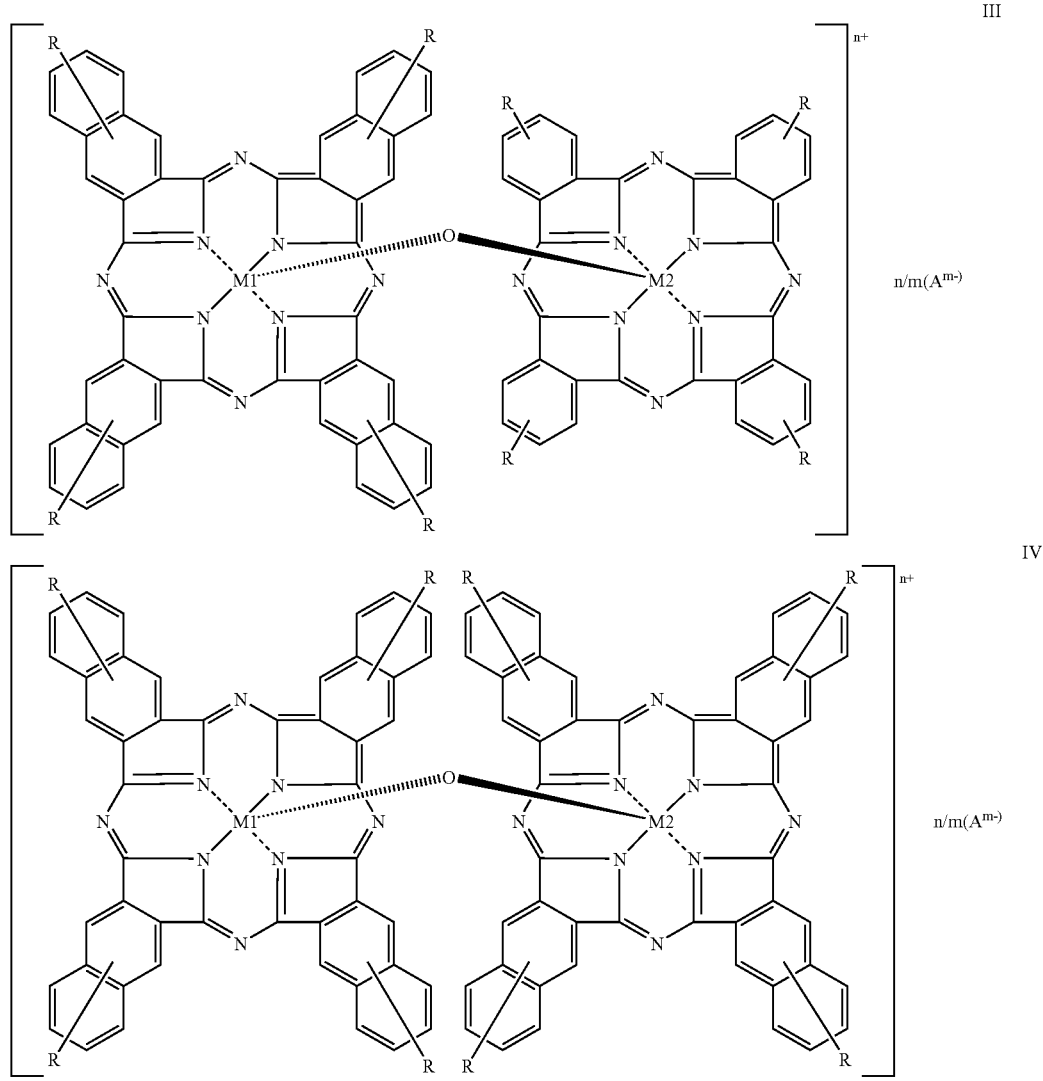

wherein M1 represents a metal atom which is able to have a valence of up to three, M2 represents a metal atom which is able to have a valence of four or five, R each independently represents one or more substituent groups and/or substituent atoms, ($A^{m-}$) represents a counteranion A having a valence of m, n/m represents the number of the counteranion, n represents an integer selected from 0 or 1 to 3 corresponding to a valence of M2, and m represents 1 or 2.

* * * * *